United States Patent
Longo et al.

(10) Patent No.: US 10,246,446 B2
(45) Date of Patent: Apr. 2, 2019

(54) BLOCKERS OF THE GROWTH HORMONE RECEPTOR IN DISEASE PREVENTION AND TREATMENT

(71) Applicant: UNIVERSITY OF SOUTHERN CALIFORNIA, Los Angeles, CA (US)

(72) Inventors: Valter D. Longo, Playa de Rey, CA (US); Priya Balasubramanian, Redondo Beach, CA (US); Nouri Neamati, Ann Arbor, MI (US); Min Wei, West Covina, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 14/913,130

(22) PCT Filed: Feb. 12, 2016

(86) PCT No.: PCT/US2016/017717
§ 371 (c)(1),
(2) Date: Feb. 19, 2016

(87) PCT Pub. No.: WO2016/130901
PCT Pub. Date: Aug. 18, 2016

(65) Prior Publication Data
US 2017/0342063 A1   Nov. 30, 2017

Related U.S. Application Data

(60) Provisional application No. 62/115,356, filed on Feb. 12, 2015.

(51) Int. Cl.
| | |
|---|---|
| *C07D 405/12* | (2006.01) |
| *C07D 405/14* | (2006.01) |
| *A61K 31/55* | (2006.01) |
| *A61K 31/422* | (2006.01) |
| *A61K 31/4155* | (2006.01) |
| *C07D 413/12* | (2006.01) |
| *A61K 45/06* | (2006.01) |
| *A61K 31/4245* | (2006.01) |
| *C07D 405/06* | (2006.01) |
| *C07D 307/68* | (2006.01) |
| *C07K 16/26* | (2006.01) |
| *C07K 16/28* | (2006.01) |
| *A61P 25/00* | (2006.01) |
| *A61P 35/00* | (2006.01) |
| *A61P 25/28* | (2006.01) |
| *A61K 39/00* | (2006.01) |

(52) U.S. Cl.
CPC ........ *C07D 413/12* (2013.01); *A61K 31/4245* (2013.01); *A61K 31/55* (2013.01); *A61K 45/06* (2013.01); *A61P 25/00* (2018.01); *A61P 35/00* (2018.01); *C07D 307/68* (2013.01); *C07D 405/06* (2013.01); *C07D 405/12* (2013.01); *C07D 405/14* (2013.01); *C07K 16/26* (2013.01); *C07K 16/2869* (2013.01); *A61K 2039/505* (2013.01); *C07K 2317/21* (2013.01); *C07K 2317/33* (2013.01); *C07K 2317/34* (2013.01); *C07K 2317/75* (2013.01); *C07K 2317/76* (2013.01)

(58) Field of Classification Search
CPC .... C07D 405/12; C07D 405/14; A61K 31/55; A61K 31/422; A61K 31/4155
USPC ........................ 540/596; 514/217.03, 217.09
See application file for complete search history.

(56) References Cited

U.S. PATENT DOCUMENTS

2004/0204368 A1   10/2004 Ohmoto et al.

FOREIGN PATENT DOCUMENTS

| WO | 2006/001770 A1 | 1/2006 |
| WO | 2009/049180 A2 | 4/2009 |
| WO | 2013/192165 A2 | 12/2013 |

OTHER PUBLICATIONS

Cecil Textbook of Medicine, edited by Bennet, J.C., and Plum F., 20th edition, vol. 1, 1004-101 O, 1996.*
Freshney et al., Culture of Animal Cells, A Manual of Basic Technique, Alan R. Liss, Inc., 1983, New York, p. 4.*
Dermeret al., Bio/Technology, 1994, 12:320.*
Golub et al., Science, 286, 531-537, 1999.*
Chemical Abstracts, Reg. Nos. 1324757-41-6, 1280496-33-4, 1203233-04-8, 1180307-90-7, 1180203-07-9, 1014381-09-9, 872319-25-0, 752215-38-6, 750624-95-4, copyright 2016, 5 pgs.
Chemical Abstract, Reg. No. 1090351, copyright 2016, 1 pg.
Chemical Abstract, Reg. No. 1169951-41-0, copyright 2016, 1 pg.
Chemical Abstract, Reg. Nos. 1011657-63-8, 949847-41-0, 949831-32-7, 926515-91-5, 872119-65-8, 3 pgs.
Rosengren, L. et al., "In vivo evaluation of a novel, orally bioavailable, small molecule growth hormone receptor antagonist," Discovery Research, Biovitrum AB, Stockholm, Sweden, Dec. 11, 2006, pp. 47-53.
International Search Report dated Aug. 25, 2016, PCT/US2016/017717 filed Feb. 12, 2016, 5 pgs.
European Search Report dated Jun. 21, 2018 for EP 16749947.4 filed Feb. 12, 2016, 10 pgs.
Rosengren, L. et al., "In vivo evaluation of a novel, orally bioavailable, small molecule growth hormone receptor antagonist," Growth Hormone and IGF Rese., v. 17, No. 1, 2007, pp. 47-53.
Extended Search Report dated Sep. 28, 2018 for EP Appn. No. 16749947.4, 13 pgs.

* cited by examiner

Primary Examiner — Venkataraman Balasubramanian
(74) Attorney, Agent, or Firm — Brooks Kushman P.C.

(57) ABSTRACT

Compounds and methods for treating diseases or conditions affected by the activity or expression of genes/proteins related to human GH, GHR, STAT5, SOCS, IGF-1, insulin are provided. Monoclonal antibodies for treating diseases or conditions related to growth hormone and growth hormone receptor activity are also provided.

11 Claims, 15 Drawing Sheets
Specification includes a Sequence Listing.

MDLCQVFLTLALAVTSSTFSGSEATPATLGKASPVLQRINPSLGTSSSGKPRFTKCRSPELE
TFSCYWTEGDNPDLKTPGSIQLYYAKRESQRQAARIAHEWTQEWKECPDYVSAGKNSC
YFNSSYTSIWIPYCIKLTTNGDLLDQKCFTVDEIVQPDPPIGLNWTLLNISLTGIRGDIQVS
WQPPPNADVLKGWIILEYEIQYKEVNESKWKVMGPIWLTYCPVYSLRMDKEHEVRVRS
RQRSFEKYSEFSEVLRVIFPQTNILEACEEDIQFPWFLIIIFGIFGVAVMLFVVIFSKQQRIKM
LILPPVPVPKIKGIDPDLLKEGKLEEVNTILGIHDNYKPDFYNDDSWVEFIELDIDEADVD
EKTEGSDTDRLLSNDHEKSAGILGAKDDDSGRTSCYDPDILDTDFHTSDMCDGTLKFRQ
SQKLNMEADLLCLDQKNLKNLPYDASLGSLHPSITQTVEENKPQPLLSSETEATHQLAST
PMSNPTSLANIDFYAQVSDITPAGGDVLSPGQKIKAGIAQGNTQREVATPCQENYSMNSA
YFCESDAKKCIAVARRMEATSCIKPSFNQEDIVITTESLTTTAQMSETADIAPDAEMSVPD
YTTVHTVQSPRGLILNATALPLPDKKNFPSSCGYVSTDQLNKIMQ

Fig. 8A

| Monoclonal Antibody | Epitope | GHR (N) | GHR (C) |
|---|---|---|---|
| 14618-1-1/C562 | SEQ ID NO 2: TEGDNPDLKTPG | 69 | 80 |
| 14618-1-3/C565 | SEQ ID NO 3: ESKWKVMGPIWL | 209 | 220 |
| 14618-1-5/C570 | SEQ ID NO 4: KLTTNGDLLDQK | 136 | 147 |
| 14618-1-6/C576 | SEQ ID NO 5: RSFEKYSEFSEV | 243 | 254 |
| 14618-1-8/C592 | SEQ ID NO 6: TVDEIVQPDPPI | 150 | 161 |
| 14618-1-4/C000 | SEQ ID NO 7: TLLNISLTGIRG | 166 | 177 |
| 14618-1-7/C579, 580, 581 | SEQ ID NO 8: EYEIQYKEVNES | 199 | 210 |
| 14618-1-9/C497 | SEQ ID NO 9: PVYSLRMDKEHE | 224 | 235 |

Fig. 10

BLOCKERS OF THE GROWTH HORMONE RECEPTOR IN DISEASE PREVENTION AND TREATMENT

CROSS-REFERENCE TO RELATED APPLICATIONS

This application is the U.S. national phase of PCT Appln. No. PCT/US2016/017717 filed Feb. 12, 2016 which claims the benefit of U.S. provisional application Ser. No. 62/115,356 filed Feb. 12, 2015, the disclosures of which are hereby incorporated in their entireties by reference herein.

STATEMENT REGARDING FEDERALLY SPONSORED RESEARCH OR DEVELOPMENT

The invention was made with Government support under Contract No. 5P01AG034906-04 awarded by the National Institute of Health. The Government has certain rights to the invention.

SEQUENCE LISTING

The text file is usc0138_ST25.txt, created Feb. 12, 2016, and of size 8 KB, filed herewith, is hereby incorporated by reference.

TECHNICAL FIELD

In at least one aspect, the present invention relates to compounds and methods for treating diseases or conditions by causing inhibition of the activity or expression of GH, GHR, STAT5, IGF-1 and/or SOCS and of proteins regulated by human GH, GHR, STAT5, SOCS, IGF-1, and insulin.

BACKGROUND

Acromegaly is a disease caused by excessive secretion of GH from pituitary adenomas. The estimated world-wide market for SOMAVERT® (pegvisomant, a human GHR antagonist) is over 160 M USD. SOMAVERT® is administered to patients who have failed pituitary adenoma surgery and are resistant to somatostatin analogs [1]. A major downside to SOMAVERT® treatment is that it is administered as a once daily injection (Pfizer). Thus a GHR blocker such as that being proposed here, that can block hGHR signaling would be very desirable in the treatment of acromegaly.

Age is a major risk factor for many types of tumors resulting in a markedly increased cancer incidence in the elderly population [2-4]. Most cancers (78%) are diagnosed in persons 55 years of age and older (source: American Cancer Society). Age is also associated with increased chemotherapy toxicity, which limits the safety and efficacy of standard chemotherapy [5-7]. In clinical reports, elderly patients experienced more myelosuppression and had a greater risk of chemotherapy-related death than younger patients in many types of cancers [6]. This poses a serious problem considering that most cancers occur in elderly individuals who are also more susceptible to chemotherapy toxicity. Although new and less toxic drugs are slowly replacing or being added to the widely used toxic chemotherapy drugs, interventions to reduce toxicity in the elderly are not established [8]. As underlined recently in *Nature Reviews in Clinical Oncology* in an article titled "Reducing the toxicity of cancer therapy: recognizing needs, taking action", development of novel strategies and drugs aimed at selective host/patient protection could reduce the side effects associated with chemotherapy treatment and also increase the therapeutic index. Because these drugs would protect against both exogenous and endogenous toxins, they would also have the potential to protect against age-related damage and diseases including cancer, diabetes and neurodegenerative diseases.

It is estimated that by 2030 roughly 20% of the American population will be comprised of individuals 65 and older (source: cdc.gov). Chronic diseases such as heart disease, cancer, Alzheimer's disease and diabetes are the most frequent causes of mortality in the elderly. About 95% of health care costs among older adults (65 and older) go towards chronic diseases and these costs are expected to increase by 25% by 2030 (CDC.gov). Thus, there is a great emphasis on preventing and/or delaying chronic health conditions in the aging population not only to improve quality of life in the elderly but also to curtail rising health care costs.

The basis for targeting the growth hormone receptor (GHR) is as follows. Mutations that cause genetic inhibition of the GH/GHR/IGF-1 lead to as much as a 50% increase in life span in mice [9-11]. Homozygous Ames dwarf mutations in the Prop-1 gene (df/df) prevent the generation of the anterior pituitary cells that produce growth hormone, thyroid stimulating hormone, and prolactin. Young adult df/df mice are approximately one third of the size of control mice but survive >50% longer [9]. This effect of dwarf mutations on life span appears to be caused by the absence of plasma GH, which stimulates the secretion of IGF-1 from liver cells [12]. In fact, IGF-1 is reduced dramatically in the plasma of df/df mice. The plasma GH deficiency appears to mediate the effects of Prop-1 (Ames dwarf) and Pit-1 (Snell dwarf) mutations on longevity, since the mice that cannot release GH in response to growth hormone releasing hormone (GHRH) also live longer [12]. Furthermore, dwarf mice with high plasma GH, but a 90% lower circulating IGF-1 (growth hormone receptor/GH binding protein knock mice, GHRKO) live longer than their wild type littermates [10]. Taken together these studies suggest that the reduction in plasma IGF-1 and probably insulin is responsible for a significant portion of the life span increase in dwarf, GH deficient, and GHR/BP null mice. In fact, mice lacking one copy of IGF-1 receptor (IGF-IR$^{+/-}$) live 33% longer than their wild type controls [11]. As observed in long-lived lower eukaryotes, the activities of antioxidant enzymes superoxide dismutases and catalase are decreased in murine hepatocytes exposed to GH or IGF-1 and in transgenic mice overexpressing GH [13, 14]. In vitro studies with fibroblasts from mutant mice with deficiencies in the GH/IGF-1 axis show increased resistance against various types of stress including UV, $H_2O_2$, paraquat, alkylating agent, heat, and cadmium [15]. In rats, IGF-1 attenuates cellular stress response and the expression of stress response proteins HSP72 and hemeoxygenase [16]. Studies by Longo and colleagues in primary neurons suggest that IGF-1 sensitizes cells to oxidative stress by a Ras/Erk-dependent mechanisms [17]. The Longo laboratory and others have described how mutations that decrease the activity of the Tor/Sch9 (homolog to mammalian AKT and S6K) pathway or of the adenylyl cyclase/cAMP/PKA pathway increase life span and stress resistance in yeast [18-20]. The increase in resistance to oxidants and heat, for example, can reach 1,000 fold in yeast with mutations in both pathways [21].

Recently, a reduction in adenylyl cyclase activity by deletion of the adenylyl cyclase 5 (AC5) gene was also shown to extend life span and increase resistance to oxidative stress in mice [22], suggesting that pathways including homologs of Akt, S6 kinase and cAMP/PKA may play a partially conserved role in the regulation of aging and stress resistance in organisms ranging from yeast to mice (FIG. 2) [23]. Analogous to the activation of yeast Sch9 and Ras by glucose, the mammalian IGF-1 receptor activates both Akt/mTOR/S6K and Ras, and regulates glucose metabolism and cellular proliferation [24]. Accumulating evidence has implicated increased IGF-1 or IGF-1 signaling as risk factors in a variety of cancers [25], suggesting that this pro-mitotic pathway can promote aging and also the damages and mutations necessary for tumorigenesis.

More recently a study of 99 living and 53 deceased Ecuadorian individuals with genetic inhibition of the GHR (Growth Hormone Receptor Deficient, GHRD) has shown that absence of GH/IGF-1 signaling protects against two major age-related diseases, cancer and diabetes [26]. GHRD individuals, who have very low IGF-1 levels appear to have a normal life span that is similar to their non-GHRD counterparts [26]. Thus inhibition of GH/IGF-1 signaling by drug interventions has the potential to be useful in reducing the incidence of cancer and diabetes particularly in families with a high incidence of these diseases. As discussed earlier, inhibition of GH/IGF-1 signaling would have many other applications: chronic treatment of acromegaly (excessive GH production) [27], differential protection against chemotoxicity [28], and oxidative stress associated with ischemia/reperfusion-induced damages [29].

The inhibition of GHR-IGF-1 signaling has also recently been shown to promote hematopoietic regeneration (Cheng et al., *Cell Stem Cell* 2014) and stem cell based regeneration of multiple systems (U.S. Pat. Appl. No. 20140227373). Moreover, the genetic inhibition of the GHR protects mice from chemotherapy-induced immune suppression (FIG. 3A) and DNA damage in bone marrow and mononuclear peripheral blood cells, in part by causing hematopoietic stem-cell dependent regeneration (FIG. 3B) (Cheng et al., *Cell Stem Cell* 2014). It has also been demonstrated that the genetic inhibition of the GHR reduces tumor growth and enhances the survival in a xenograft tumor model in mice (FIG. 4). Finally, Parrella et al. have recently shown that inhibition of GH-IGF-1 signaling protects from the age-dependent cognitive impairment and pathology in an Alzheimer's disease mouse model (Parrella et al., Aging Cell. 2013 April; 12(2) 257-68).

Accordingly, there is a need for developing new disease treatment protocols based on the inhibition of GHR-IGF-1 signaling.

SUMMARY

The present invention solves one or more problems of the prior art by providing in at least one embodiment, a compound for treating diseases or conditions by causing inhibition of the activity or expression of GH, GHR, STAT5, IGF-1 and/or SOCS and of proteins regulated by human GH, GHR, STAT5, SOCS, IGF-1, and insulin is provided. The compound of this embodiment has formula I:

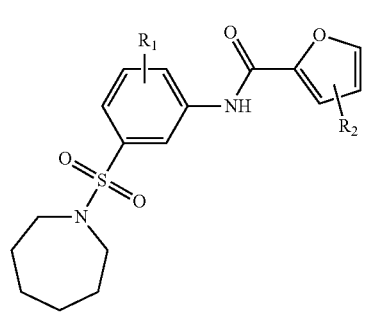

wherein:

$R_1$ is hydrogen, $NO_2$, $SO_3H$, $NH_2$, $C_{1-8}$ alkyl, or halogen, and $R_2$ is hydrogen, $NO_2$, $SO_3H$, $NH_2$, $C_{1-8}$ alkyl, $C_{1-8}$ alkyl, or halogen.

In another embodiment, a compound that is useful for the treatment of diseases or conditions by causing inhibition of the activity or expression of GH, GHR, STAT5, IGF-1 and/or SOCS and of proteins regulated by human GH, GHR, STAT5, SOCS, IGF-1, and insulin is provided. The compound of this embodiment has formula II:

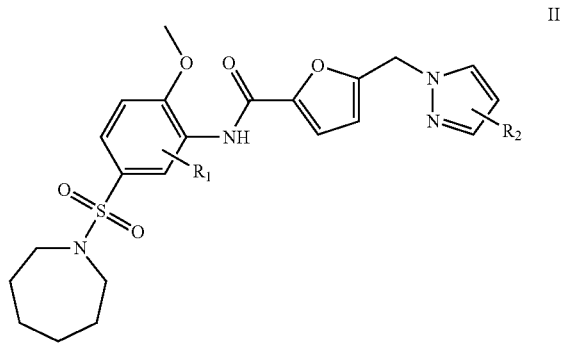

wherein:

$R_1$ is hydrogen, $NO_2$, $SO_3H$, $NH_2$, $C_{1-8}$ alkyl, or halogen, and $R_2$ is hydrogen, $NO_2$, $SO_3H$, $NH_2$, $C_{1-8}$ alkyl, or halogen.

In another embodiment, a compound that is useful for the treatment of diseases or conditions by causing inhibition of the activity or expression of GH, GHR, STAT5, IGF-1 and/or SOCS and of proteins regulated by human GH, GHR, STAT5, SOCS, IGF-1, and insulin is provided. The compound of this embodiment has formula III:

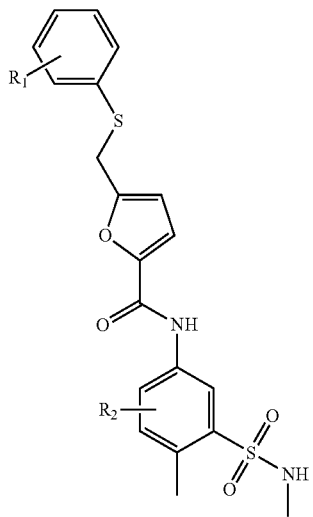

III wherein:

R₁ is hydrogen, NO$_2$, SO$_3$H, NH$_2$, C$_{1-8}$ alkyl, or halogen, and

R$_2$ is hydrogen, NO$_2$, SO$_3$H, NH$_2$, C$_{1-8}$ alkyl, or halogen.

In another embodiment, a compound that is useful for the treatment of diseases or conditions by causing inhibition of the activity or expression of GH, GHR, STAT5, IGF-1 and/or SOCS and of proteins regulated by human GH, GHR, STAT5, SOCS, IGF-1, and insulin is provided. The compound of this embodiment has formula IV:

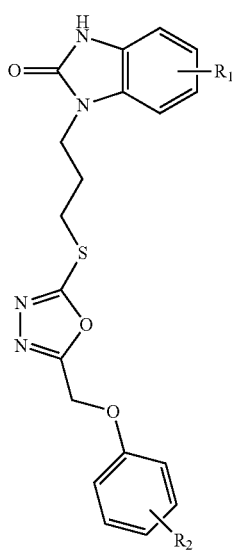

IV wherein:

R₁ is hydrogen, NO$_2$, SO$_3$H, NH$_2$, C$_{1-8}$ alkyl, or halogen, and

R$_2$ is hydrogen, NO$_2$, SO$_3$H, NH$_2$, C$_{1-8}$ alkyl, or halogen.

Advantageously, the compounds set forth above in formulae I-IV are useful for treating diseases or conditions selected from the group consisting of acromegaly, cancer, diabetes, Alzheimer's, and aging. The compounds and inhibition of the pathways by the compounds are also useful to protect from chemotherapy toxicity and promote multi-system stem cell based regeneration and to treat conditions and diseases benefitting from stem cell-based regeneration (C. W. Cheng et al. Cell Stem Cell, 2014; 14 (6): 810 DOI: 10.1016/j.stem.2014.04.014)

In another embodiment, a method for treating diseases related to growth hormone activity is provided. In this embodiment, inhibitory anti-growth hormone receptor (GHR) monoclonal antibodies are used to reduce growth hormone (GH) action and consequently the Insulin Growth Factor 1 (IGF-1) activity in vivo. Because of the pro-growth effect of GH and IGF-1 on certain tumor cells and because GH/IGF-1 signaling plays an important role in mammalian aging, this invention has a great potential to provide an antibody-based drug to: a) attenuate/delay the growth of GH- and/or IGF-1 dependent tumor cells; b) induce organism-level protection against acute stress, e.g. chemotherapy-associated toxicity to normal tissue, radiation induced cellular toxicity, or other toxic drugs and compounds; c) enhance the therapeutic index of existing chemotherapy; d) modulate risk factors associated with age-related diseases; e) attenuate/delay changes in biomarkers associated with aging; f) promote multi-system stem cell-based regeneration; g) reduce or delay the incidence of diabetes and Alzheimer and retard their progression.

BRIEF DESCRIPTION OF THE DRAWINGS

FIG. 8A. Mouse growth hormone receptor protein sequence. SEQ ID NO: 1 is depicted: Residue 1-24 (italic), Signal peptide; Residue 25-264 (underlined), GH binding protein; Residue 274-297 (bold), Transmembrane domain.

FIG. 10. Monoclonal antibodies and their target epitopes used in the experiments of FIGS. 8 and 9.

DETAILED DESCRIPTION

Figure 1:
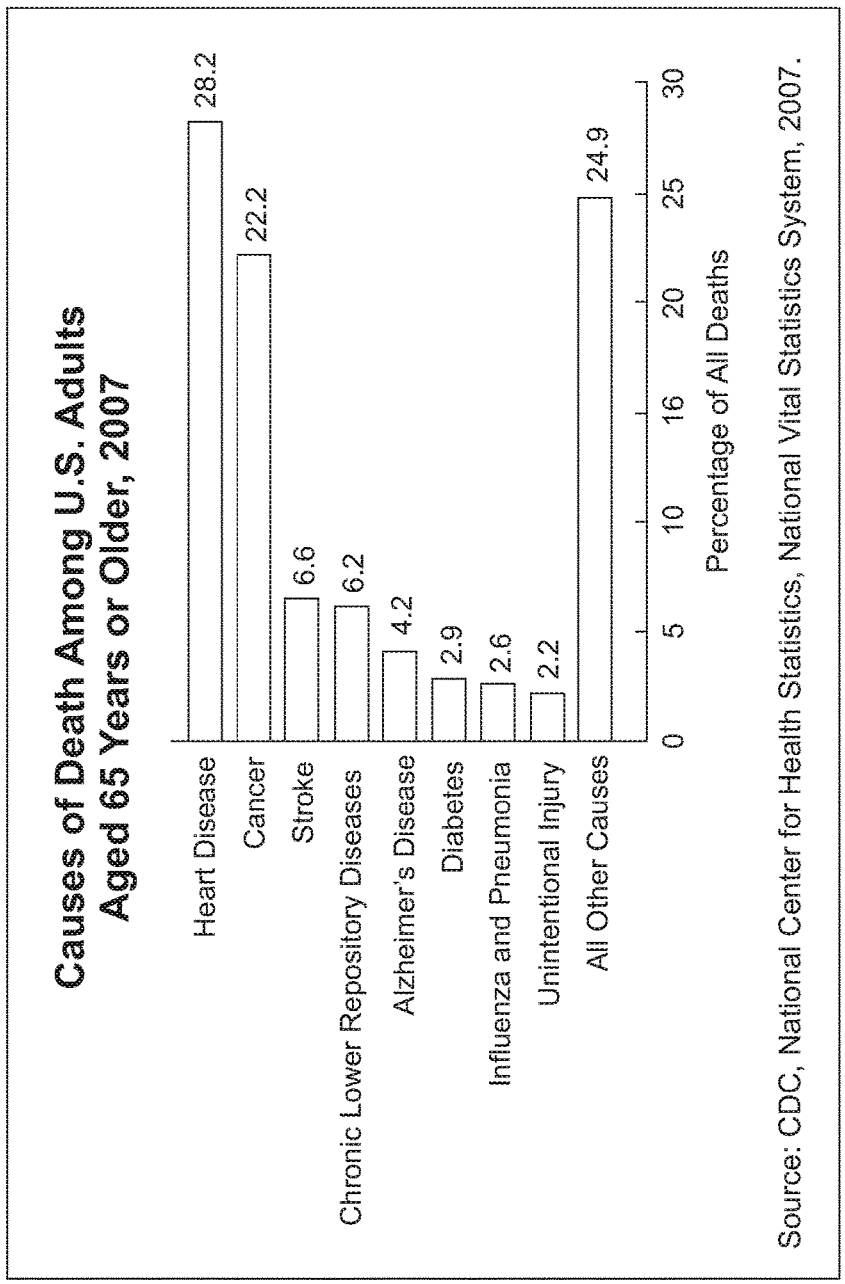
FIG. 1. Bar chart showing causes of death in the elderly (from the CDC, National Center for Health Statistics, National Vital Statistics System, 2007).
Figure 2:
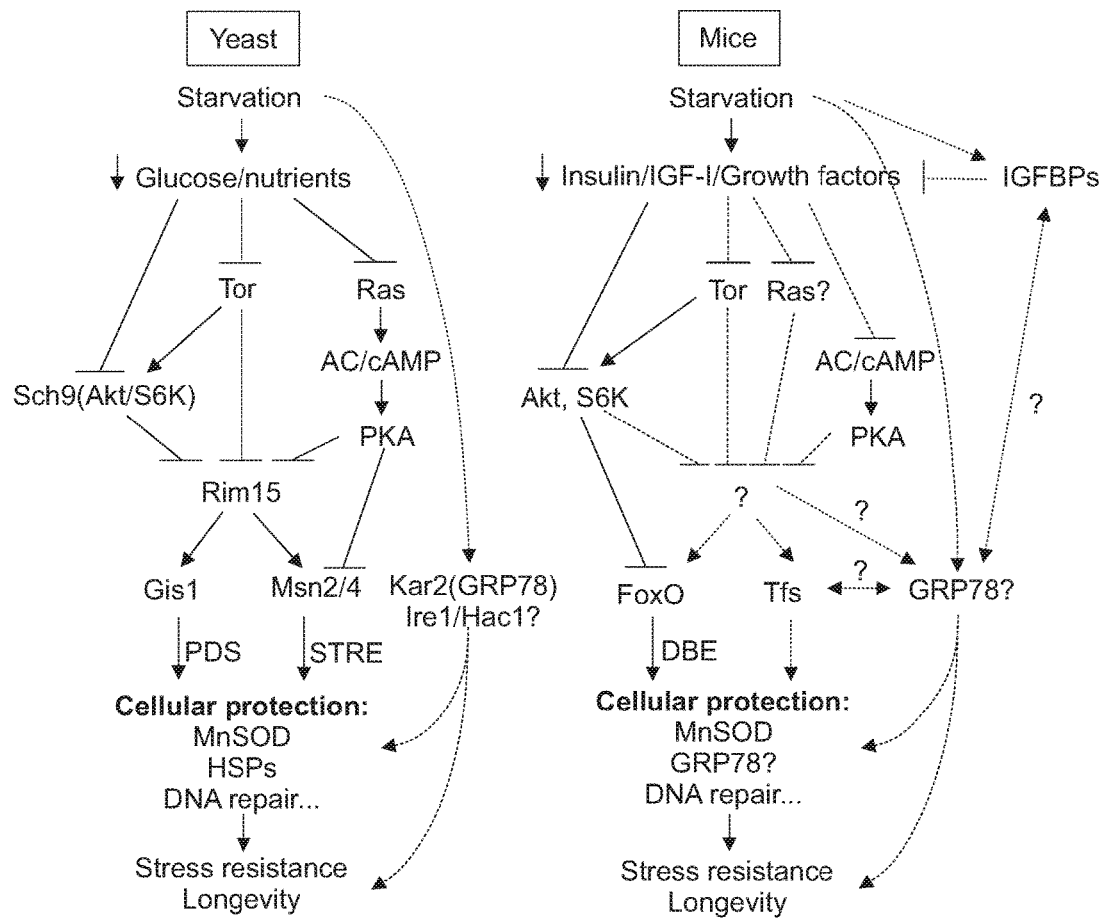
FIG. 2. Similar pathways regulate longevity and resistance to stress in yeast and mice (adapted from Longo, 2003).
Figure 3A:
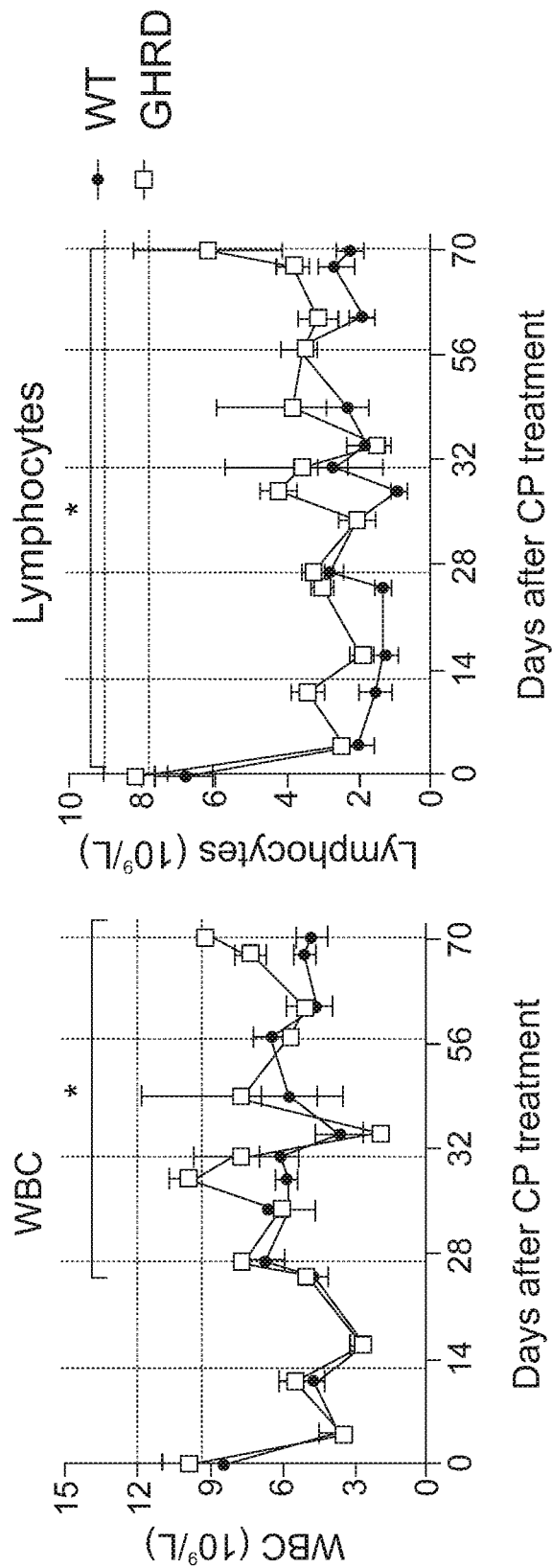
FIG. 3A. Genetic inhibition of the GHR protects bone marrow (BM) and mononuclear peripheral blood (PB) cells against chemotoxicity in mice. Total white blood cell (WBC) and lymphocyte counts in the peripheral blood of GHRD mice and their wild type littermates (WT); each point represents the mean±s.e.m; vertical dashed lines indicate cyclophosphamide (CP) treatments; horizontal dashed lines indicate baseline levels; *$p<0.05$, Two-way ANOVA for recovery phases.
Figure 3B:
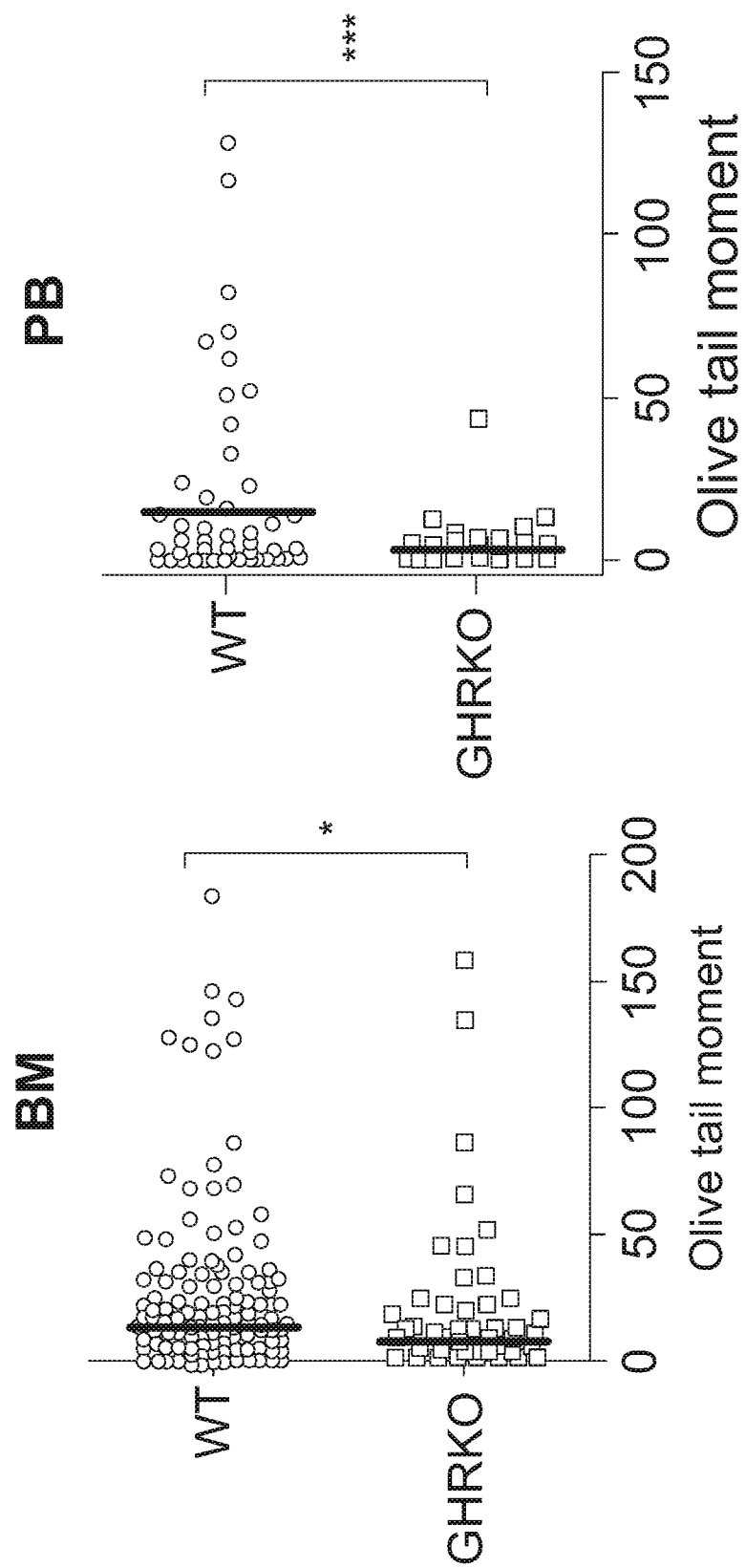
FIG. 3B. GHR knockout (GHRKO) mice and their age-matched wild type (WT) littermates were treated with six cycles of cyclophosphamide (CP) (200 mg/kg, i.p.). DNA damage (olive tail moment) were measured with Comet Assay in bone marrow (BM) and mononuclear peripheral blood (PB) cells after 6 cycles of CP treatments.
Figure 4A:
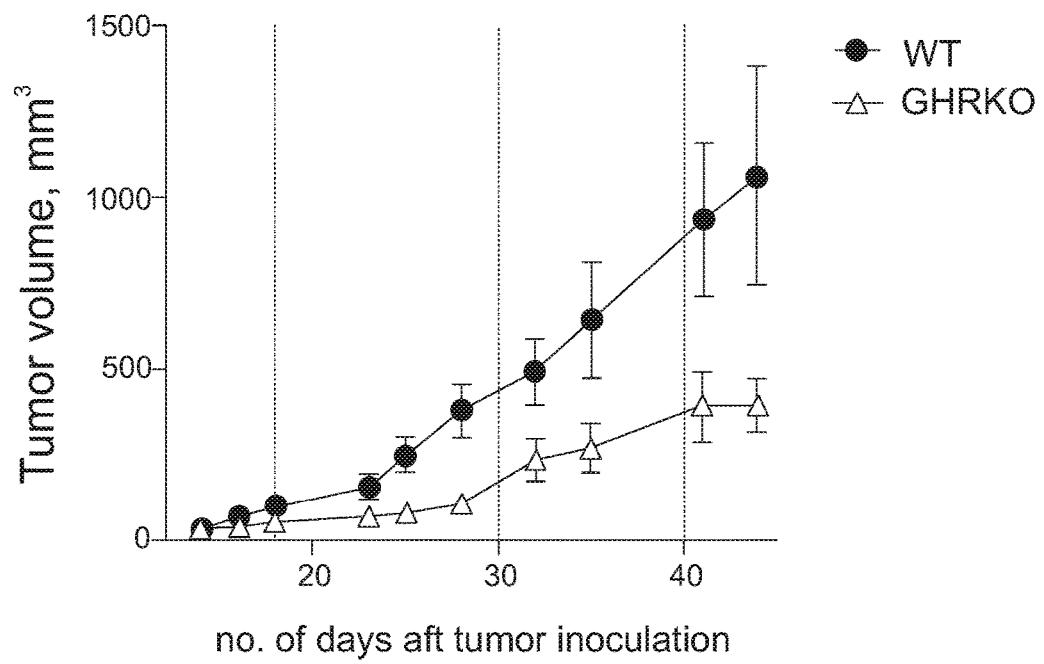
FIG. 4A. Genetic inhibition of GHR reduces tumor growth and enhances tumor-bearing survival in a xenograft tumor model in mice. GHRKO mice and their age-matched wide type littermates (WT), were inoculated with B16Flu melanoma subcutaneously and subjected to Cyclophosphamide (CP) treatment (i.p. 200 mg/kg body weight, indicated with vertical dashed lines). Tumor growth over 3 cycles of CP treatment.
Figure 4B:
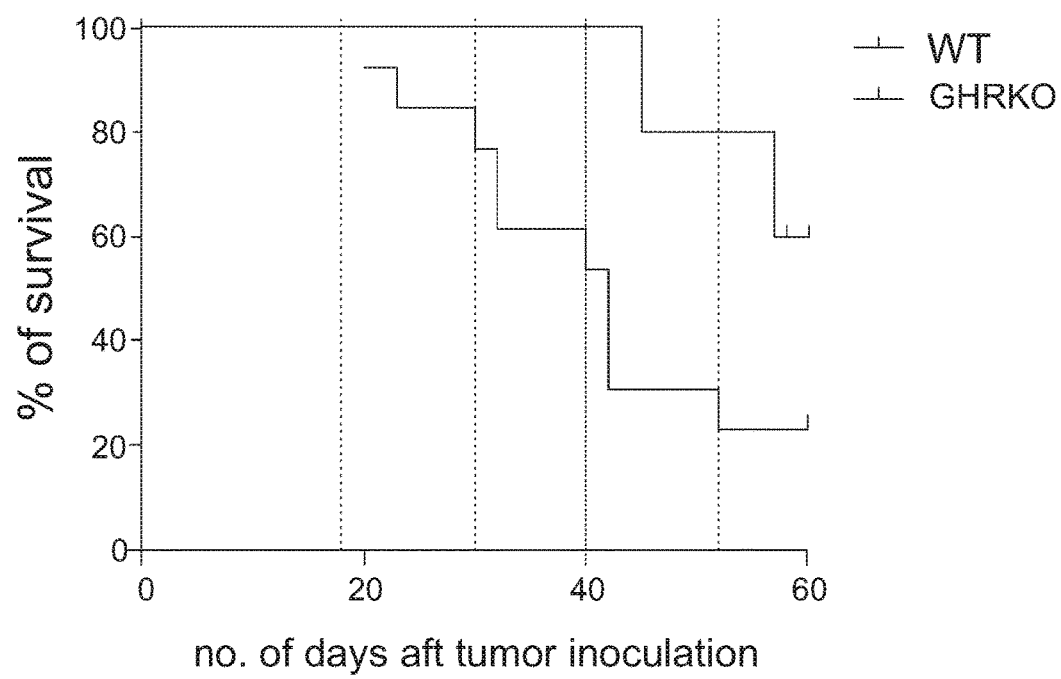
FIG. 4B. Tumor-bearing survival of the GHRKO and WT mice. Genetic inhibition of GHR reduces tumor growth and enhances tumor-bearing survival in a xenograft tumor model in mice. GHRKO mice and their age-matched wide type littermates (WT), were inoculated with B16Flu melanoma subcutaneously and subjected to cyclophosphamide (CP) treatment (i.p. 200 mg/kg body weight, indicated with vertical dashed lines).

Reference will now be made in detail to presently preferred compositions, embodiments, and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; "R" groups include H, $C_{1-10}$ alkyl, $C_{2-10}$ alkenyl, $C_{6-14}$ aryl (e.g., phenyl, halo, or $C_{4-14}$ heteroaryl; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation and applies mutatis mutandis to normal grammatical variations of the initially defined abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

The term "subject" refers to a human or animal, including all mammals such as primates (particularly higher primates), sheep, dog, rodents (e.g., mouse or rat), guinea pig, goat, pig, cat, rabbit, and cow.

Abbreviation:
AKT, V-Akt Murine Thymoma Viral Oncogene Homolog, Protein Kinase B.
B16Flu, Green fluorescent protein (GFP) expressing B16 mouse malignant melanoma cells.
BM, Bone marrow.
cAMP, Cyclic adenosine monophosphate.
CMV, Cytomegalovirus immediate-early promoter.
CP, Cyclophosphamide.
df/df, Ames dwarf.
DNA, Deoxyribonucleic Acid.
ERK, Extracellular signal-regulated kinases.
FBS, Fetal bovine serum.
GH, Growth hormone.
GHA, growth hormone antagonist.
GHR, Growth hormone Receptor.
GHR/BP, Growth hormone Receptor/growth hormone binding protein.
GHRD, Growth hormone Receptor deficiency.
GHRH, Growth hormone releasing hormone.
GHRKO, Growth hormone Receptor knockout.
HEK293, Human embryonic kidney cell 293.
hGH, Human growth hormone.
HSP72, Heat shock protein 72.
IGF-1, Insulin-like growth factor 1.
IGF-1 receptor.
MEK, Mitogen-activated protein kinase kinase.
PB, Peripheral blood.
PBMC, Peripheral blood mononuclear cells.
Pit-1, POU domain, class 1, transcription factor 1.
PKA, Protein kinase A.
Prop-1, Prophet Of Pit1.
RAS, Rat sarcoma.
RLU, Relative light units.
S6K, Ribosomal Protein S6 Kinase.
Sch9, Serine/threonine-protein kinase SCH9.
SOCS, Suppressor of cytokine signaling.
STAT5, Signal Transducer and Activator of Transcription 5.
Tor, Target of rapamycin
UV, Ultraviolet.
WBC, White blood cells.
WT, Wild type.

In various embodiments of the invention, compounds and methods for alleviating symptoms of various diseases, conditions, and treatments are provided. In particular, these compounds and methods can be used to treat acromegaly, chemotherapy or other therapies involving toxins that damage normal cells, cancer, diabetes, immunodepression, immunosuppression, immunosenescence, immunodeficiency, Alzheimer's, aging, and diseases and conditions benefitting from cellular and tissue regeneration. Typically, the compounds and methods of the invention are used to treat ailments related to or caused by the expression (or over expression) of GH, GHR, STAT5, IGF-1 and/or SOCS and of proteins regulated by human GH, GHR, STAT5, SOCS, IGF-1, and insulin.

The present invention solves one or more problems of the prior art by providing in at least one embodiment, a compound for treating diseases or conditions by causing inhibition of the activity or expression of GH, GHR, STAT5, IGF-1 and/or SOCS and of proteins regulated by human GH, GHR, STAT5, SOCS, IGF-1, and insulin is provided. The compound of this embodiment has formula I:

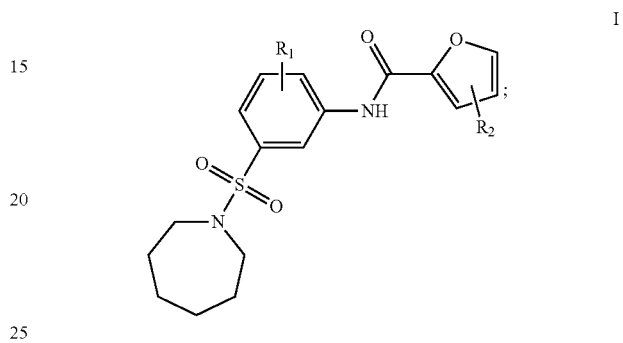

or a pharmaceutically acceptable salt thereof;
wherein:
$R_1$ is hydrogen, $NO_2$, $SO_3H$, $NH_2$, $C_{1-8}$ alkyl, or halogen, and
$R_2$ is hydrogen, $NO_2$, $SO_3H$, $NH_2$, $C_{1-8}$ alkyl, or halogen. In a refinement, $R_1$ and $R_2$ are each independently hydrogen, methyl, ethyl, n-propyl, isopropyl, n-butyl, sec-butyl, isobutyl, t-butyl, or phenyl.

In another embodiment, a compound that is useful for the treatment of diseases or conditions by causing inhibition of the activity or expression of GH, GHR, STAT5, IGF-1 and/or SOCS and of proteins regulated by human GH, GHR, STAT5, SOCS, IGF-1, and insulin is provided. The compound of this embodiment has formula II:

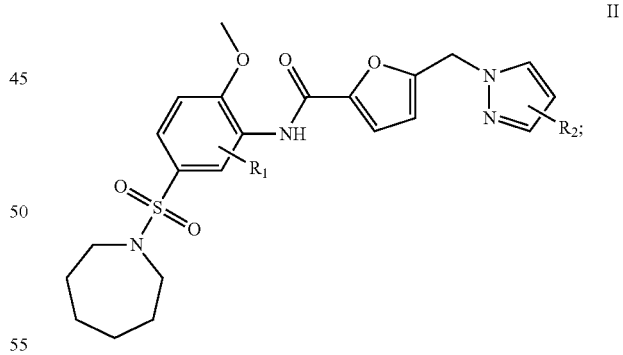

or a pharmaceutically acceptable salt thereof;
wherein:
$R_1$ is hydrogen, $NO_2$, $SO_3H$, $NH_2$, $C_{1-8}$ alkyl, or halogen, and
$R_2$ is hydrogen, $NO_2$, $SO_3H$, $NH_2$, $C_{1-8}$ alkyl, or halogen. In a refinement, $R_1$ and $R_2$ are each independently hydrogen, methyl, ethyl, n-propyl, isopropyl, n-butyl, sec-butyl, isobutyl, t-butyl, or phenyl.

In another embodiment, a compound that is useful for the treatment of diseases or conditions by causing inhibition of the activity or expression of GH, GHR, STAT5, IGF-1 and/or SOCS and of proteins regulated by human GH, GHR, STAT5, SOCS, IGF-1, and insulin is provided. The compound of this embodiment has formula III:

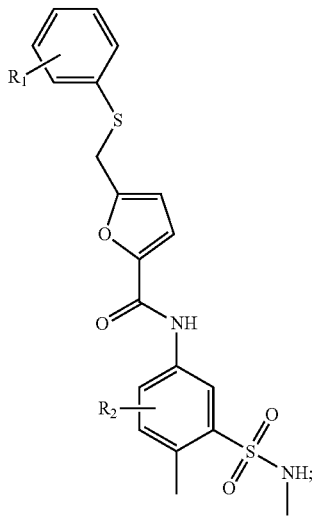

or a pharmaceutically acceptable salt thereof;
wherein:
$R_1$ is hydrogen, $NO_2$, $SO_3H$, $NH_2$, $C_{1-8}$ alkyl, or halogen, and
$R_2$ is hydrogen, $NO_2$, $SO_3H$, $NH_2$, $C_{1-8}$ alkyl, or halogen. In a refinement, $R_1$ and $R_2$ are each independently hydrogen, methyl, ethyl, n-propyl, isopropyl, n-butyl, sec-butyl, isobutyl, t-butyl, or phenyl.

In another embodiment, a compound that is useful for the treatment of diseases or conditions by causing inhibition of the activity or expression of GH, GHR, STAT5, IGF-1 and/or SOCS and/or of proteins regulated by human GH, GHR, STAT5, SOCS, IGF-1, and insulin is provided. The compound of this embodiment has formula IV:

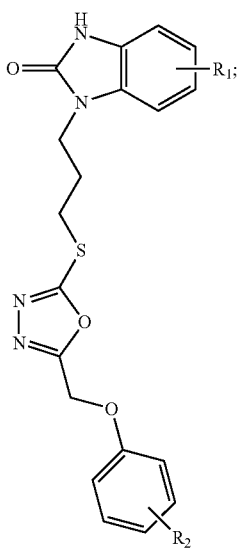

or a pharmaceutically acceptable salt thereof;
wherein:
$R_1$ is hydrogen, $NO_2$, $SO_3H$, $NH_2$, $C_{1-8}$ alkyl, or halogen, and
$R_2$ is hydrogen, $NO_2$, $SO_3H$, $NH_2$, $C_{1-8}$ alkyl, or halogen. In a refinement, $R_1$ and $R_2$ are each independently hydrogen, methyl, ethyl, n-propyl, isopropyl, n-butyl, sec-butyl, isobutyl, t-butyl, or phenyl.

In still another embodiment, the compounds set forth above in formulae I-IV are uses to treating diseases or conditions selected from the group consisting of acromegaly, cancer, diabetes, Alzheimer's, and aging. The compounds and inhibition of the pathways by the compounds are also useful to protect from chemotherapy toxicity and promote multi-system stem cell based regeneration (C. W. Cheng et al. Cell Stem Cell, 2014; 14 (6): 810 DOI: 10.1016/j.stem.2014.04.014). In this regard, a method for treating diseases or conditions with alterations in signaling genes related to human GH, GHR, STAT5, and SOCS is provided. In this context, the term "related to" means that the signaling genes are part or a signaling pathway that leads to expression of GH, GHR, STAT5, and SOCS. This includes a step of identifying a subject having a disease or condition in which signaling genes or the proteins which they encode related to human GH, GHR, STAT5, and SOCS or contribute to the disease or condition. A therapeutically effective amount of a compound selected from the group consisting of compounds having formulae I-IV and combinations thereof is administered to the subject.

The compounds set forth above are administered to the subject in a therapeutically effective amount so that symptoms of acromegaly, cancer, diabetes, Alzheimer's, or aging are alleviated. In a refinement, such amounts will generally be from about 0.1 to about 300 mg per kg of subject body weight depending on the specific compound being used and on its effects on the activity or expression of GH, GHR, STAT5, SOCS, IGF-1 and insulin. Typical doses are from about 1 to about 5000 mg per day for an adult subject of normal weight.

The compounds of the present invention may form pharmaceutically acceptable salts with both organic and inorganic acids or bases. For example, the acid addition salts of the basic compounds are prepared either by dissolving the free base in aqueous or aqueous alcohol solution or other suitable solvents containing the appropriate acid and isolating the salt by evaporating the solution. Examples of pharmaceutically acceptable salts are hydrochlorides, hydrobromides, hydrosulfates, etc. as well as sodium, potassium, and magnesium, etc. salts. The compounds having formula I-IV can contain one or several asymmetric carbon atoms. The invention includes the individual diastereomers or enantiomers, and the mixtures thereof. The individual diastereomers or enantiomers may be prepared or isolated by methods already well-known in the art.

Pharmaceutical compositions include the compounds set forth above or a salt therefore and a pharmaceutical carrier. Typically the pharmaceutical compositions are divided into dosage units. Examples of dosage unit forms include, but are not limited to, pills, powders, tablets, capsules, aqueous and nonaqueous oral solutions and suspensions, and parenteral solutions.

Examples of suitable pharmaceutical carriers include, but are not limited to, water, sugars (e.g., lactose and sucrose), starches (e.g., corn starch and potato starch), cellulose derivatives (e.g., sodium carboxymethyl cellulose, and methyl cellulose), gelatin, talc, stearic acid, magnesium stearate, vegetable oils (e.g., peanut oil, cottonseed oil, sesame oil, olive oil, etc.), propylene glycol, glycerin, sorbitol, polyethylene glycol, water, agar, alginic acid, saline, and other pharmaceutically acceptable materials.

The percentage of the active ingredients in the pharmaceutical compositions can be varied within wide limits. In one refinement, a concentration of at least 10% in a solid composition and at least 2% in a primary liquid composition is used. The most useful compositions have a higher percentage of the active which a much higher proportion of the active ingredient is present.

Routes of administration of the subject compound or its salts are oral or parenteral. For example, a useful intravenous dose is between 1 and 50 mg and a useful oral dosage is between 5 and 800 mg.

In still another embodiment, a method for treating diseases related to or caused by growth hormone activity is provided. A subject having a disease or condition caused by the activity of growth hormone or genes regulated by it including GHR, IGF-1 and insulin is identified. A therapeutically effective amount of antibodies that target the growth hormone receptor and/or the growth hormone is administered to the subject. In this embodiment, inhibitory anti-growth hormone (anti-GH) or anti growth hormone receptor (anti-GHR) monoclonal antibodies are used to reduce growth hormone (GH) action and consequently the Insulin Growth Factor 1 (IGF-1) and insulin activity. Because of the pro-growth effect of GH and IGF-1 on certain tumor cells and because GH/IGF-1 signaling plays an important role in mammalian aging, this invention has a great potential to provide an antibody-based drug to: a) attenuate/delay the growth of GH- and/or IGF-1 dependent tumor cells; b) induce organism-level protection against acute stress, e.g. chemotherapy- or cancer therapy-associated toxicity to normal tissue, radiation induced cellular toxicity, or other toxic drugs and compounds; c) enhance the therapeutic index of existing chemotherapy and other cancer therapies; d) modulate risk factors associated with age-related diseases; e) attenuate/delay changes in biomarkers associated with aging; f) promote multi-system stem cell-based regeneration; g) reduce or delay the incidence of Alzheimer and retard its progression.

The following examples illustrate the various embodiments of the present invention. Those skilled in the art will recognize many variations that are within the spirit of the present invention and scope of the claims.

Assay procedures: The following assays are used to screen for activity: 1. STAT5 phosphorylation assay and 2. Luciferase reporter assays.

The JAK/STAT signaling pathway is the principal signaling mechanism for a variety of growth factors and cytokines. In the growth hormone signaling pathway, dimerization of the GHR in response to GH binding leads to the activation of JAK by transphosphorylation. Activated JAK phosphorylates STAT5, which can then enter the nucleus and activate transcription of target genes. Inhibition of STAT5 phosphorylation will be used to analyze GHR antagonistic properties of the test compounds.

Mouse L fibroblasts engineered to express mouse GHR were obtained from Dr. John Kopchick. Serum starved L cells (0.5% FBS for 24 hours) were pre-treated for 30 minutes with 10 µM of each compound identified as a hit from the luciferase assays. Following this, cells were treated with 5 or 10 nM hGH for 10 minutes. Cells were collected and processed for western blotting with phospho-STAT5 and total STAT5 antibodies (Cell Signaling). The GHR antagonist, G120K is used as a positive control. Band intensity was analyzed using ImageJ and STAT5 phosphorylation normalized to total STAT5 levels. Compounds that inhibited STAT5 phosphorylation were selected for further drug optimization.

Figure 7:
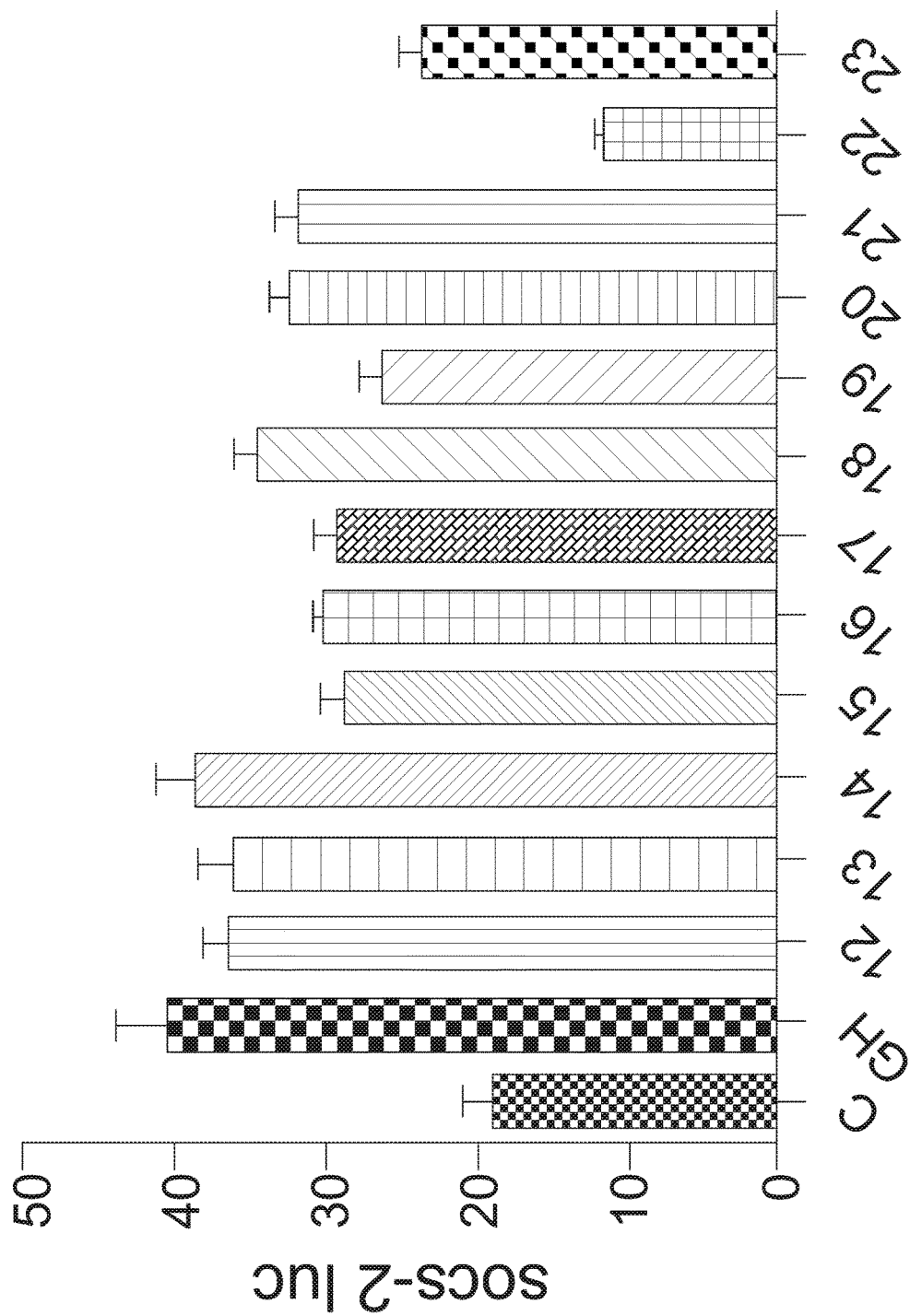
FIG. 7. High throughput screening (HTS) platform for the identification of GHR inhibitors. Mouse L cells expressing human GHR were transfected with SOCS2 reporter luciferase plasmids. Cells were serum starved, pre-treated with test compounds (numbered as shown) and then GH. Data are normalized to CMV renilla luciferase and expressed as relative light units (RLU).
Figure 8B:
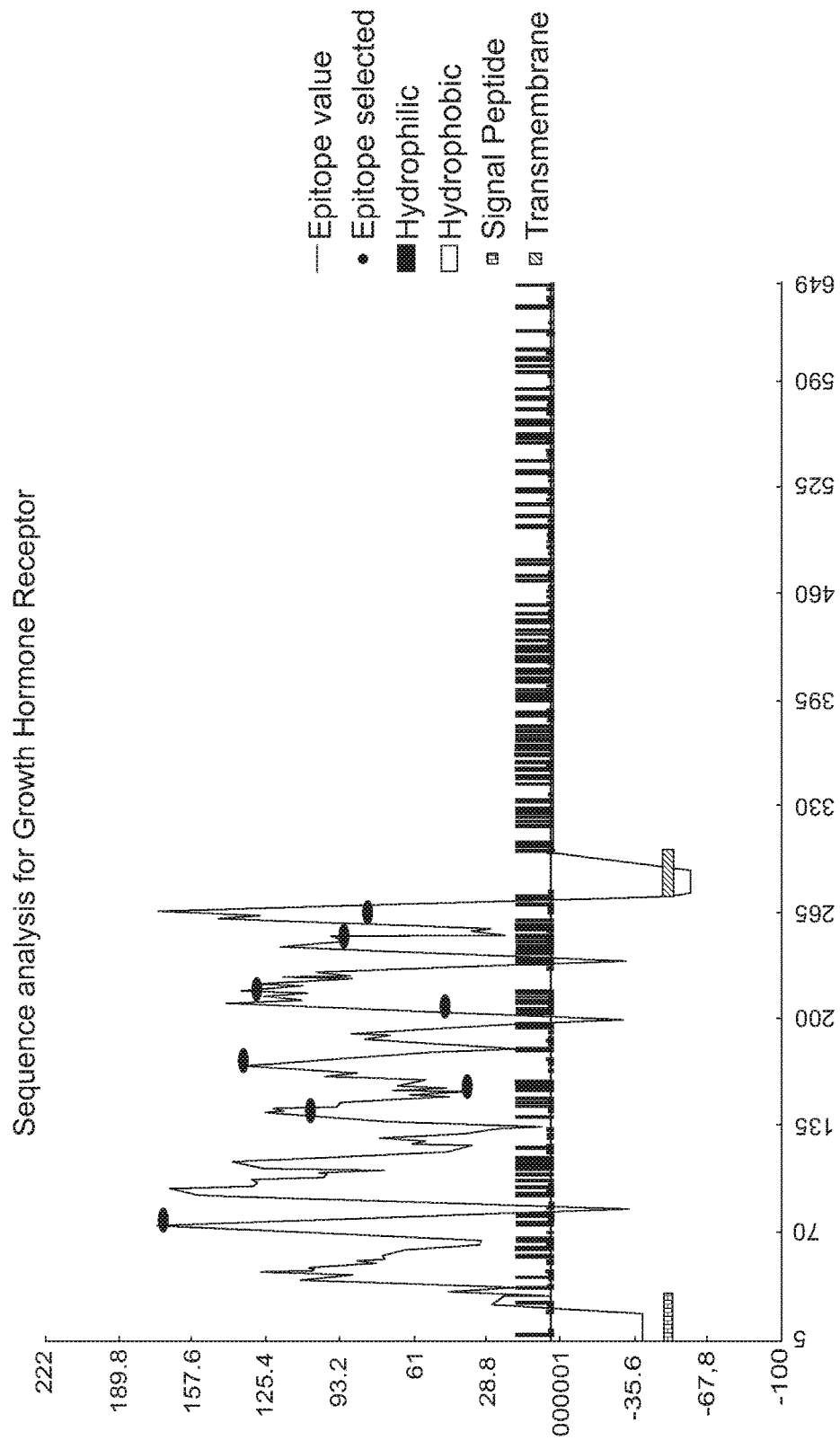
FIG. 8B. Structure analysis of mouse growth hormone receptor for epitope selection. Epitope score was determined by a proprietary algorithm.

In order to perform high throughput screening (HTS) for inhibitors of GHR, HEK293 cell lines permanently transfected were established with a luciferase reporter driven by either c-fos or SOCS2 promoter (FIG. 7).

The SOCS (Suppressor of Cytokine Signaling) proteins are induced by GH and act as negative regulators of cytokine signaling pathways [30, 31]. Expression of the proto-oncogene c-fos is also induced by GH via the Ras/MEK/ERK pathway [32]. Luciferase reporter constructs where the luciferase gene is under the control of promoters of either SOCS2 or c-fos have been stably transfected into human embryonic kidney, HEK293 cells. Cells were serum starved (0.5% FBS) for 24 hours to prevent interference by other growth factors and then treated with 5 or 10 nM hGH (established in dose response studies) and 10 µM of each test compound for 24 hours. This is followed by lysis and analysis of luciferase activity using the luciferase reporter assay (Promega). Each compound is tested in triplicate in a 96 well plate format.

Figure 5B:
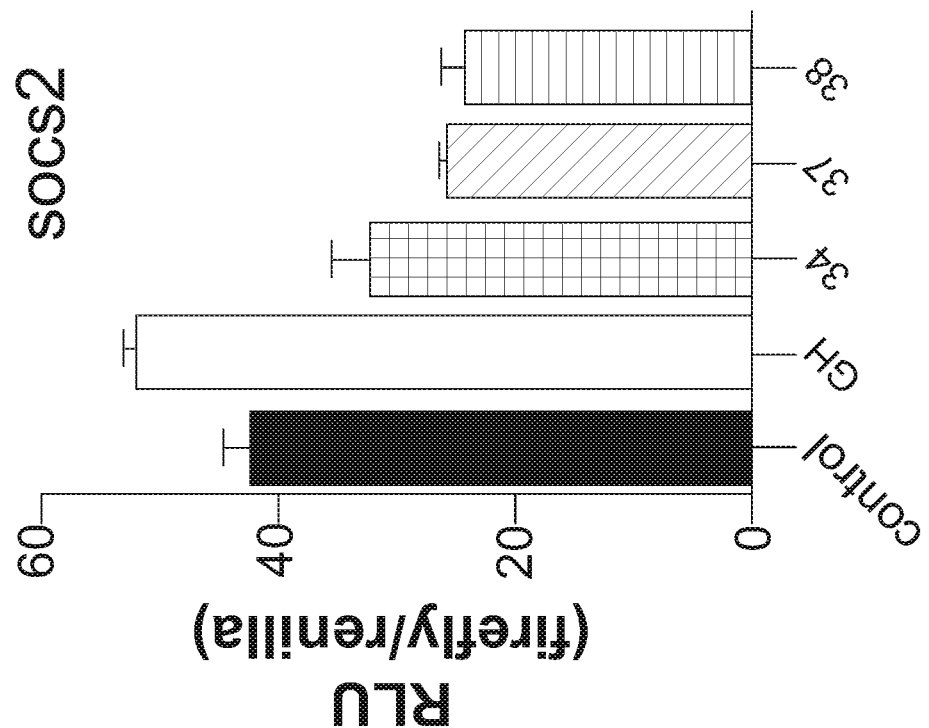
FIG. 5B. Lead compounds (#34, 37, 38) identified by luciferase reporter assays. Mouse L cells expressing human GHR were transfected with c-fos or SOCS2 reporter luciferase plasmids. Cells were serum starved, then incubated with test compounds (#34, 37, 38) before GH treatment. Data were normalized to co-transfected CMV-driven renilla luciferase and expressed as relative light units (RLU). (B) SOCS2 reporter luciferase activity.
Figure 5A:
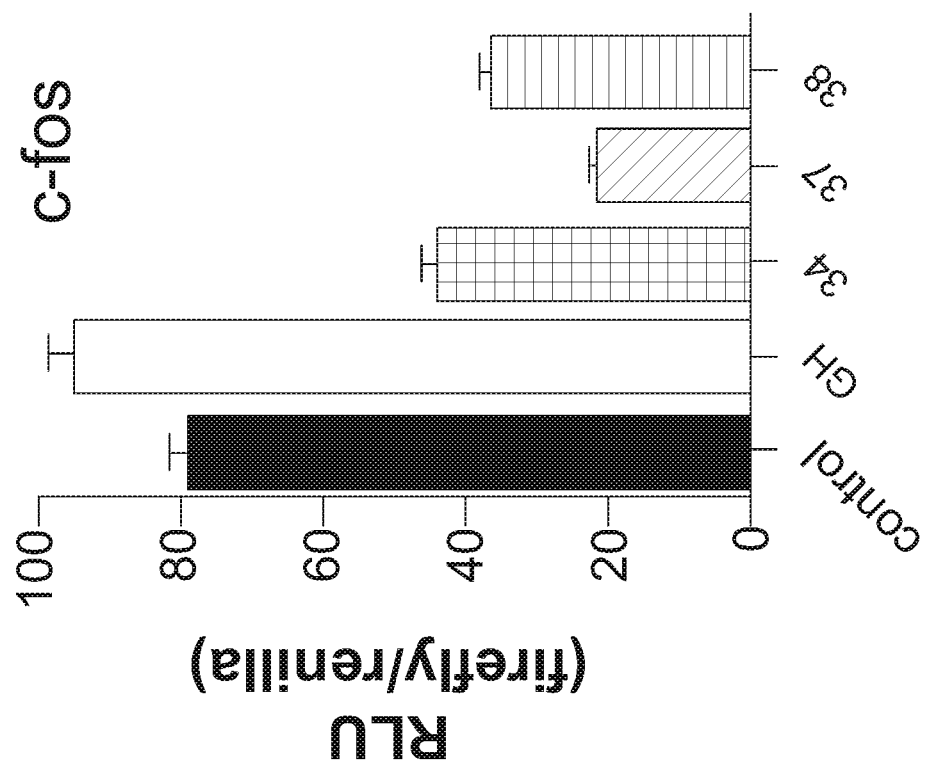
FIG. 5A. Lead compounds (#34, 37, 38) identified by luciferase reporter assays. Mouse L cells expressing human GHR were transfected with c-fos or SOCS2 reporter luciferase plasmids. Cells were serum starved, incubated with test compounds (#34, 37, 38) and then treated with GH. Data are normalized to co-transfected CMV-driven renilla luciferase and expressed as relative light units (RLU). (A) c-fos reporter luciferase activity.
Figure 6:
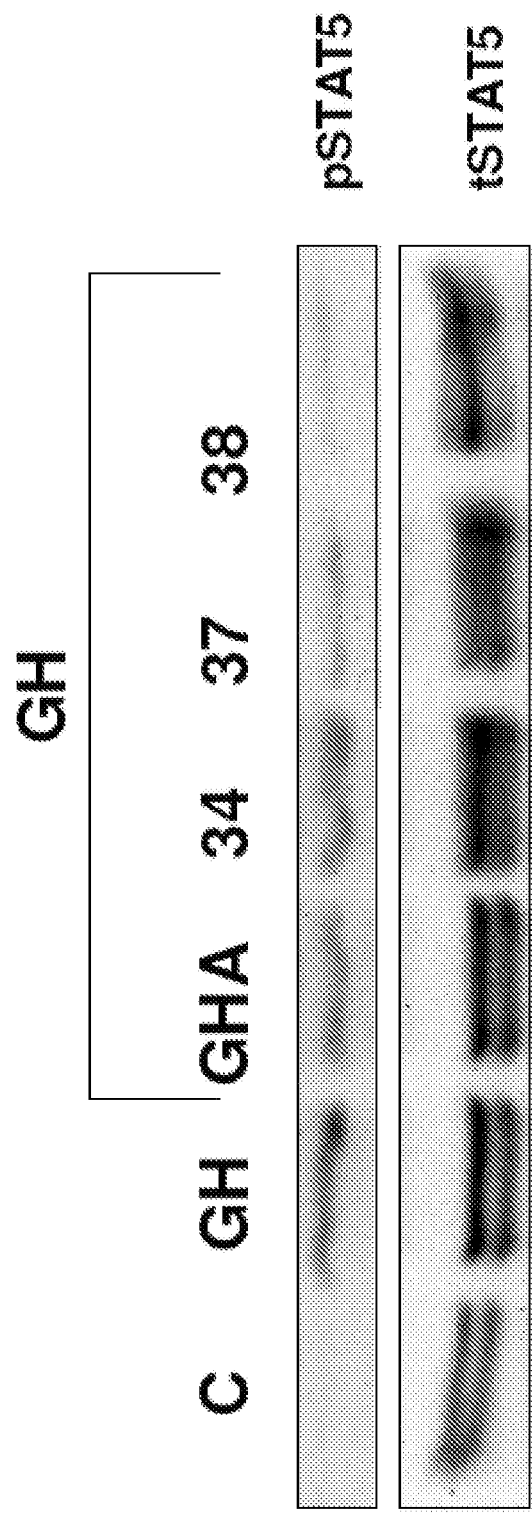
FIG. 6. Lead compounds inhibit STAT5 phosphorylation. (A) Mouse L cells were incubated in 0.5% serum for 24 hours. Cells were treated with compounds 34, 37 or 38 for 30 min prior to 5 nM hGH treatment. The growth hormone antagonist (GHA) was used as a positive control.

Three potential lead compounds were identified that inhibit GH-GHR signaling (DSR 34, 37 and 38) (FIGS. 5A and B) using our primary screening process. FIG. 5 shows luciferase reporter assays for the three compounds, DSR 34, 37 and 38. All three compounds inhibited GH induced increase in c-fos and SOCS2 reporter activity (FIGS. 5A and B). Further, the compounds could inhibit reporter activities to below that of untreated controls, c-fos reporter activity is 57%, 27% and 46.5% of untreated controls whereas SOCS2 reporter activity is 76%, 61% and 57% of untreated controls for compounds 34, 37 and 38 respectively. These compounds were also tested for their ability to inhibit GH induced phosphorylation of STAT5 in mouse L cells expressing human GHR (FIG. 6). All three compounds are able to inhibit phosphorylation of STAT5 (FIG. 6). These compounds were further optimized and generated an additional lead (compound 22) as shown below (FIG. 7).

The structure of compounds 22, 34, 37, and 38 are as follows:

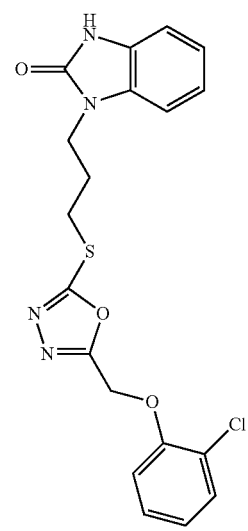

Molecular Weight: 416.88
B63H1 (Compound 22)

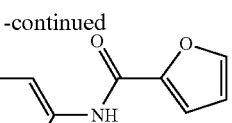

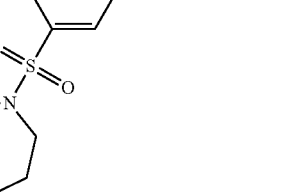

B4B7 (Compd 34)
Molecular Weight: 348.42

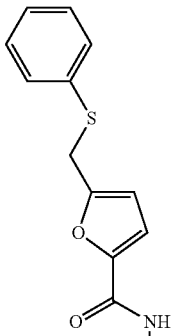

B4G1 (Compd 37)
Molecular Weight: 416.51

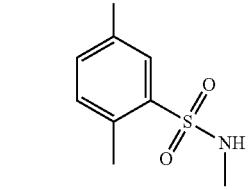

Figure 12A:
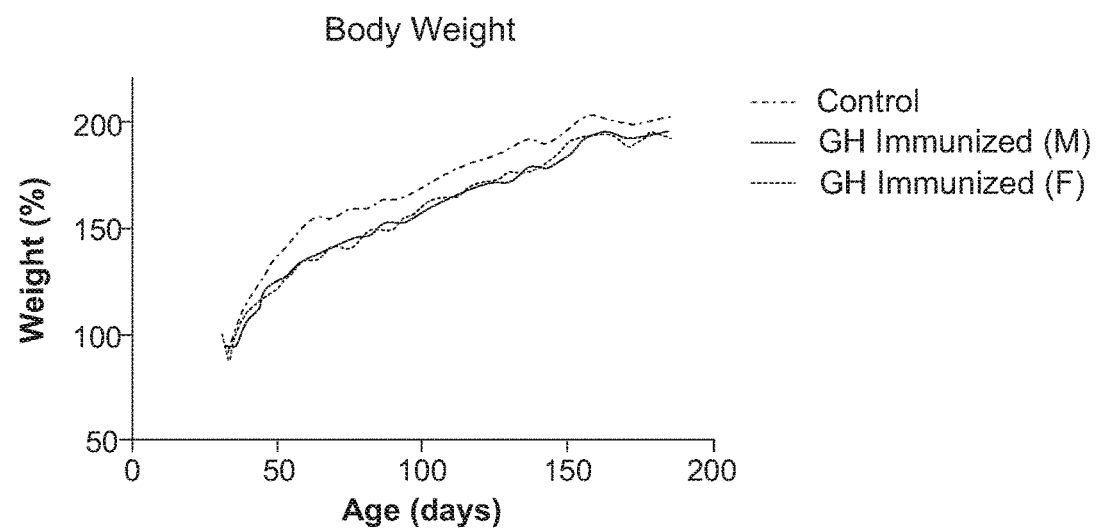
FIG. 12A. Mice expressing a novel inhibitory growth hormone antibody described in this application were protected against chemotherapy. 4 week old CD1 male (M) and female (F) mice were immunized with human GH with booster doses injected at week 10. A) The mice exhibited a loss in body weight compared with controls indicating that they had generated anti-human GH antibodies that cross-reacted with mouse GH and in turn slowed growth.
Figure 12B:
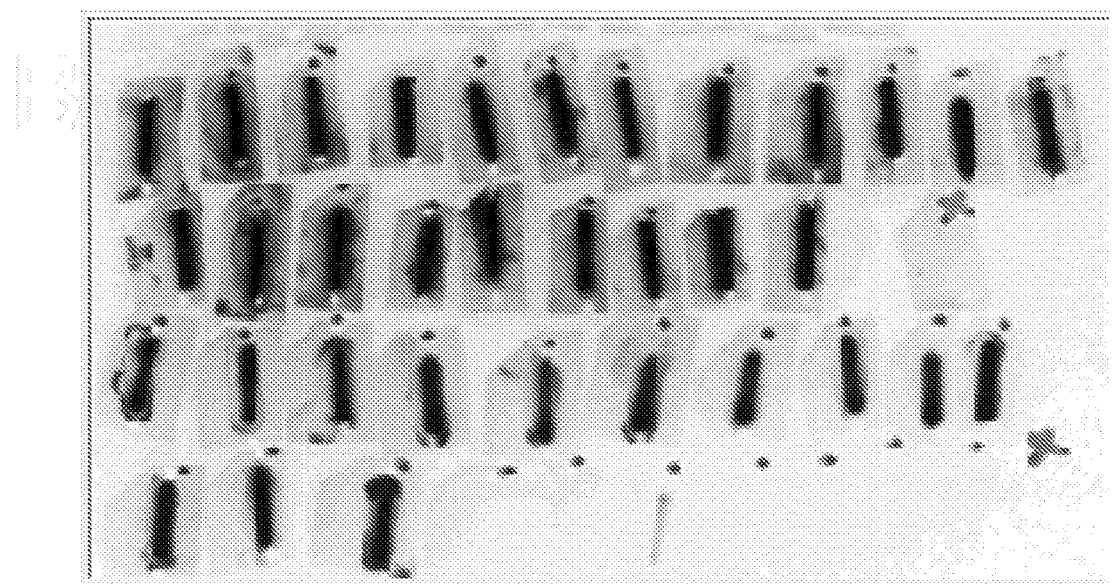
FIG. 12B. Slot-blot analysis of serum from immunized mice showed reactivity to human GH in 34 out of 40 mice confirming that antibodies had been generated.
Figure 12C:
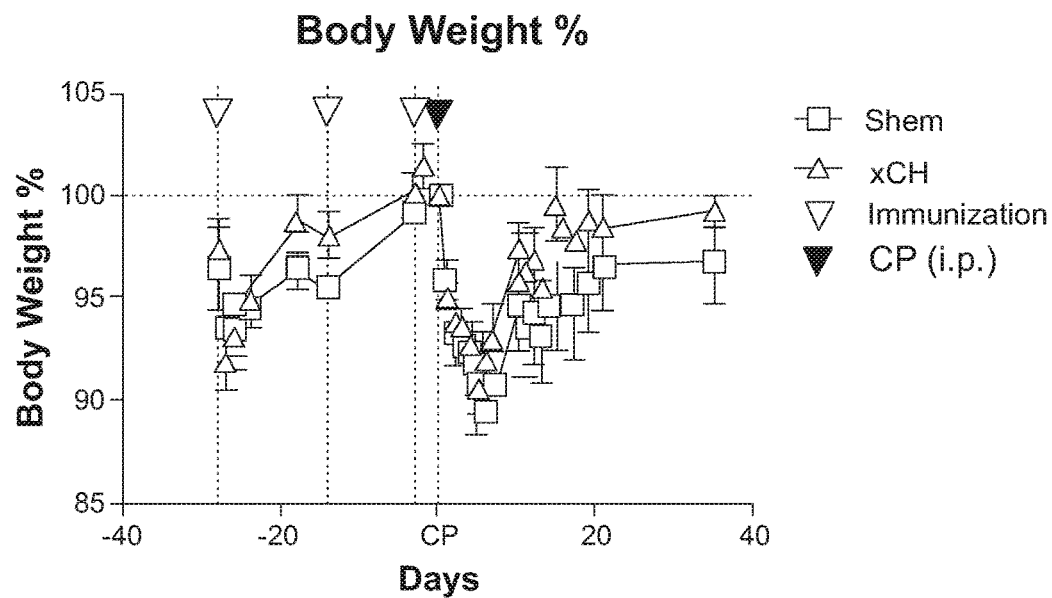
FIG. 12C. GH-immunized mice that were given a booster dose of human GH immunization at 6 months and then treated with cyclophosphamide (CP) as shown were better able than controls (non-immunized) to regain body weight.
Figure 12D:
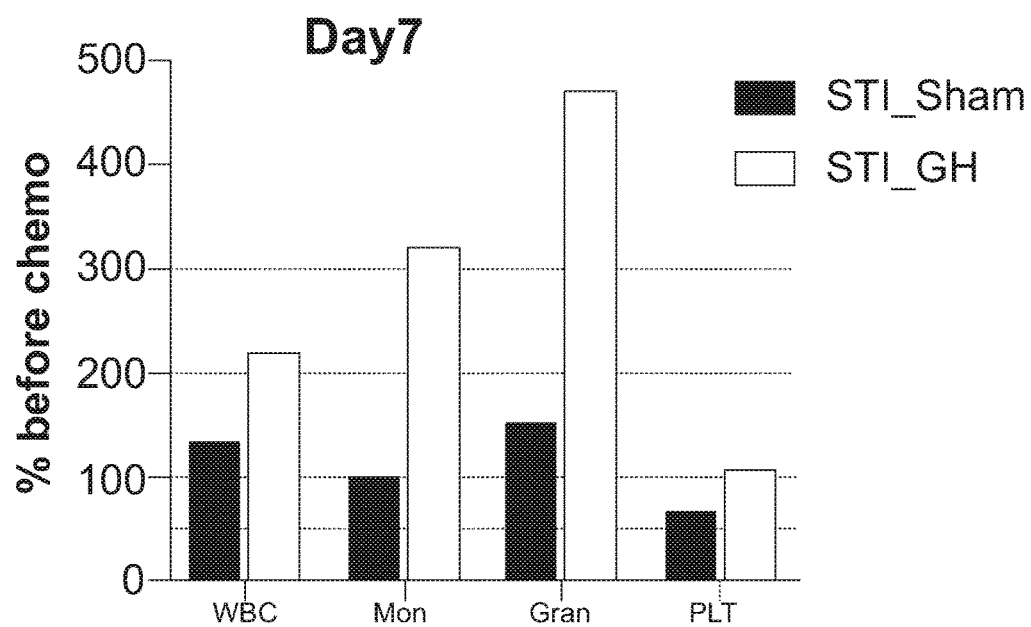
FIG. 12D. Complete blood counts also indicated that GH-immunized mice showed better blood cell profile 7 days after cyclophosphamide (CP) treatment.

B5E8 (Compd)
Molecular Weight: 458.53 or pharmaceutically acceptable salts thereof,

To test whether a reduction in GH/IGF-1 signaling by inhibiting GH using anti GH antibodies would also protect mice from chemotherapy toxicity, antibodies against mouse Growth Hormone were generated. Four (4) week old CD1 male and female mice were immunized with human GH with booster doses injected at 10 weeks. The mice exhibit a loss in body weight compared with controls indicating that they had generated anti-human GH antibodies that cross-reacted with mouse GH and in turn slowed growth (FIG. 12A). Slot-blot analysis of serum from immunized mice showed reactivity with hGH in 34/40 mice confirming that antibodies were generated (FIG. 12B). Mice that were given a booster dose of hGH at 6 months and then treated with cyclophosphamide (CP) as shown were better able than controls to regain body weight (FIG. 12C). Complete blood counts also indicated that these mice were more resistant to CP toxicity (FIG. 12D). STI indicates short-term immunization.

Figure 9:
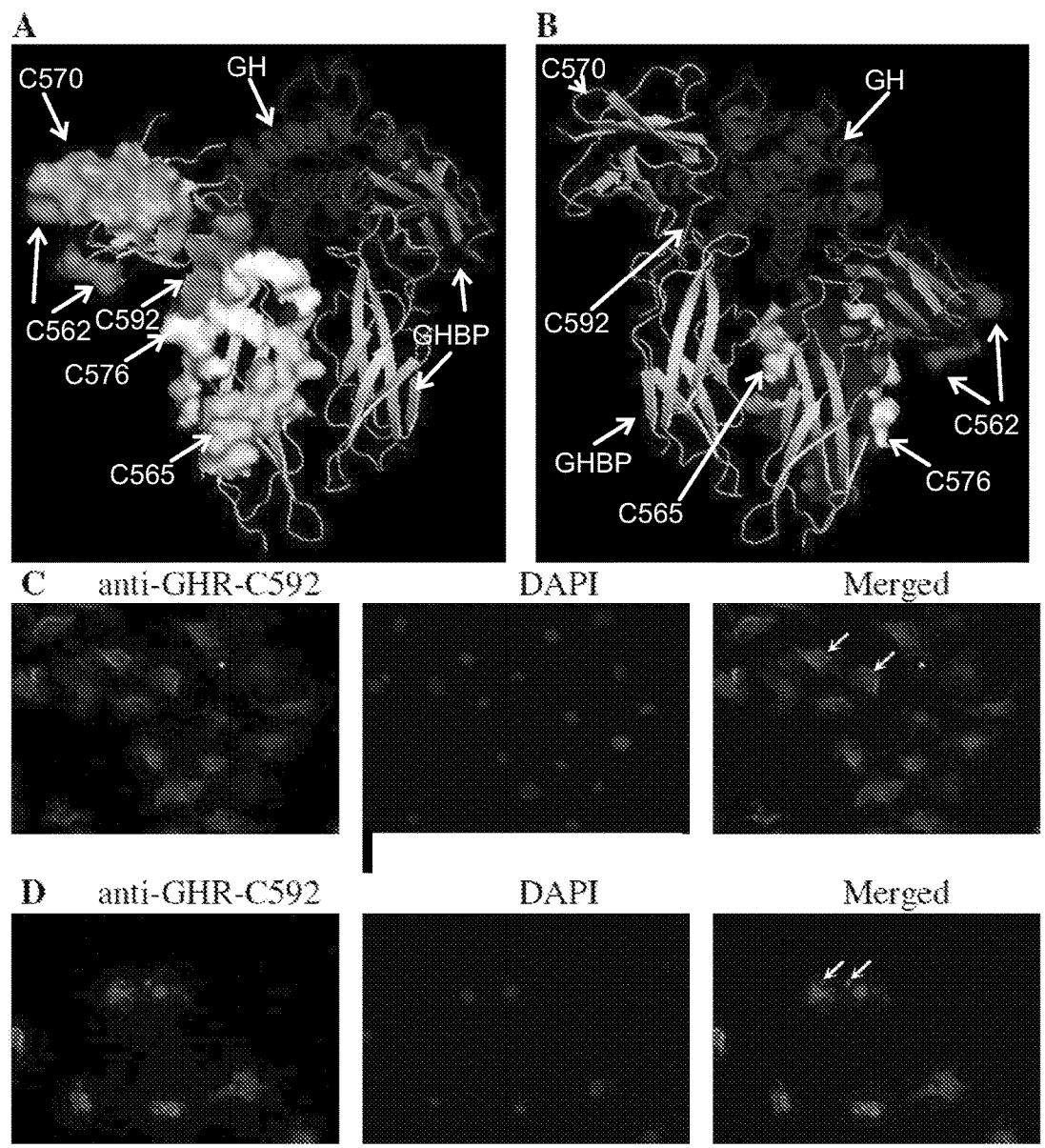
FIG. 9A. Complex of human growth hormone (GH) with its soluble binding protein (GHBP) (PDB-1HWG, visualized by PyMOL). A) Surface plot of the 5 selected epitopes (human homologous regions).
FIG. 9B. Ribbon plot of the 5 selected epitopes. Dark Blue: GH; Green, GHBP; regions shaded in purple (C562), light brown (C570), red (C592), white (C576) and turquoise blue (C565) indicate the selected epitopes that are targeted by monoclonal antibodies. Note, since only the human GH-GHR complex crystal structure is available, highlighted regions are the human equivalent regions of selected mouse GHR epitopes.
FIG. 9C. Monoclonal anti-GHR antibody (C592) specifically recognizes membrane-bound GHR (indicated by arrows).
FIG. 9D. High concentration of monoclonal anti-GHR antibody (C592) treatment leads to GHR clustering and endocytosis (indicated by arrows).
Figure 11A:
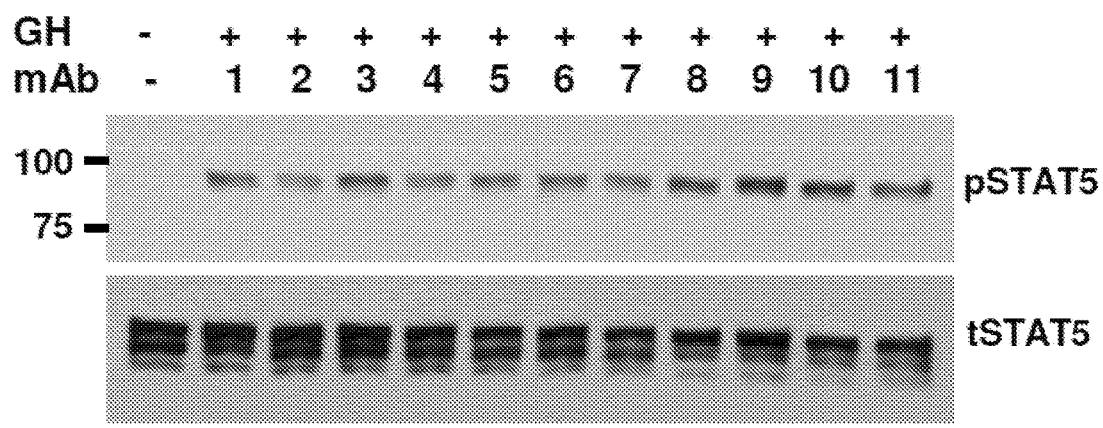
FIG. 11A. Screening of antagonistic or agonistic monoclonal antibodies against GHR. A). Mouse L cells were cultured to 80-90% confluency. Cells were then switched to DMEM with low glucose (0.5 g/L) and low FBS (0.5%) for 24 hours. Cells were incubated with monoclonal antibodies (indicated by serial numbers) for 1 hour, then treated with 5 nM Growth Hormone (GH) for 5 minutes, and assayed for STAT5 phosphorylation by Western Blot. STAT5 phosphorylation levels were normalized to total STAT5 and data are shown as percentage of no antibody treatment.
Figure 11B:
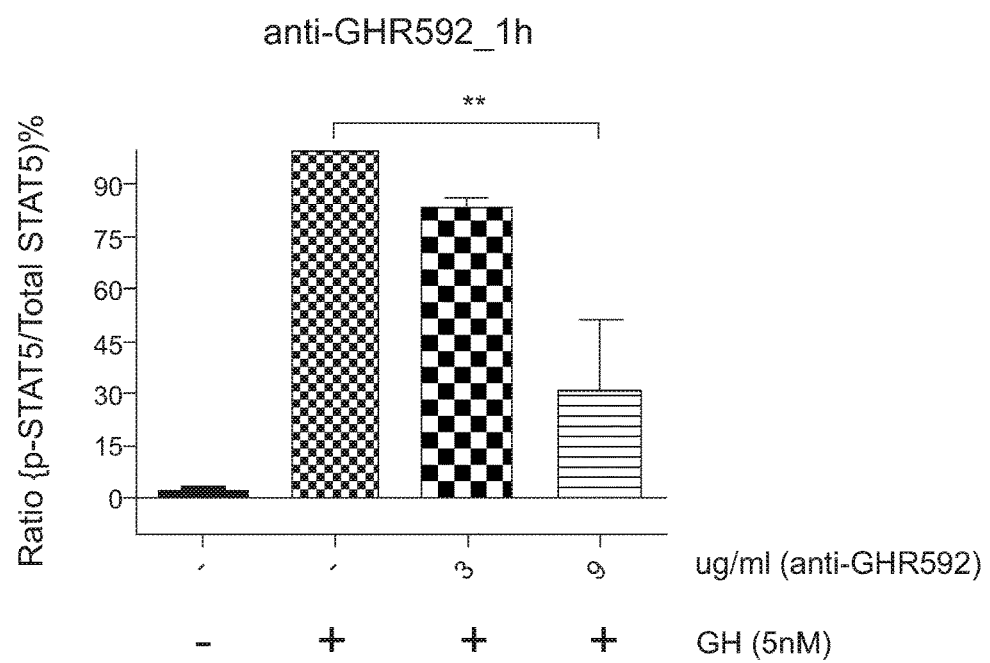
FIG. 11B. Downregulation of the GH induced phosphorylation of STAT5 by monoclonal antibody C592.

Monoclonal antibodies against various regions of the mouse GHR extracellular domain were developed. Growth hormone binds asymmetrically to the growth hormone receptor homodimer, leading to a rotation of the GHR subunits relative to each other. The current understanding of GH-GHR binding suggests that this receptor dimer conformation change is propagated through the transmembrane domain and lead to signal transduction to downstream tyrosine kinase. Depending on the epitope location and binding affinity, the binding of monoclonal antibodies can lead to receptor conformation change, aggregation, and protein-protein interaction alteration that result in either stimulatory or inhibitory effects on GHR (see FIG. 11). For example, monoclonal antibody C562 targets the N-terminal region of the GHR (FIGS. 9 and 10, target peptide-SEQ ID NO 2: TEGDNPDLKTPG, lavender shaded), with is approximate to the GH binding site and thus interferes ligand-receptor interaction; monoclonal antibody C565 binds GHR in a region (FIGS. 9 and 10, target peptide-SEQ ID NO 3: ESKWKVMGPIWL, aqua blue shaded) that may interfere both the dimerization of GHR subunits and the re-orientation of the subunits after GH binding; monoclonal antibody C592 targets the GHR region (FIGS. 9 and 10, target peptide-SEQ ID NO 6: TVDEIVQPDPPI, red shade) that sits in a "hinge" of the GHR extracellular domain. C592 binding may interfere GH binding and promote GHR clustering, endocytosis and degradation (FIGS. 9C and D). These antagonistic and agonistic monoclonal antibodies and their derivatives (e.g. Fab, F(ab')$_2$ preparations) could be potent therapeutic agents in modulating GH-GHR action in vivo. Therefore, novel and effective antibodies binding to the GHR to affect its activity have been described.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

REFERENCES

1. Kopchick, J. J., et al., *Growth hormone receptor antagonists: discovery, development, and use in patients with acromegaly*. Endocr Rev, 2002. 23(5): p. 623-46.
2. DePinho, R. A., *The age of cancer*. Nature, 2000. 408 (6809): p. 248-54.
3. Jemal, A., et at, *Cancer statistics, 2008*. CA Cancer J Clin, 2008. 58(2): p. 71-96.
4. Wedding, U., L. Pientka, and K. Hoffken, *Quality-of-life in elderly patients with cancer: a short review*. Eur J Cancer, 2007. 43(15): p. 2203-10.
5. Balducci, L. and M. Extermann, *Management of cancer in the older person: a practical approach*. Oncologist, 2000. 5(3): p. 224-37.
6. Minami, H., et al., *Comparison of pharmacokinetics and pharmacodynamics of docetaxel and Cisplatin in elderly and non-elderly patients: why is toxicity increased in elderly patients?* J Clin Oncol, 2004. 22(14): p. 2901-8.

7. Wedding, U., et al., *Tolerance to chemotherapy in elderly patients with cancer.* Cancer Control, 2007. 14(1): p. 44-56.
8. Repetto, L., *Greater risks of chemotherapy toxicity in elderly patients with cancer.* J Support Oncol, 2003. 1(4 Suppl 2): p. 18-24.
9. Brown-Borg, H. M., et al., *Dwarf mice and the ageing process.* Nature, 1996. 384(6604): p. 33.
10. Coschigano, K. T., et al., *Assessment of growth parameters and life span of GHRIBP gene-disrupted mice.* Endocrinology, 2000. 141(7): p. 2608-13.
11. Holzenberger, M., et al., *IGF-1 receptor regulates lifespan and resistance to oxidative stress in mice.* Nature, 2003. 421(6919): p. 182-7.
12. Flurkey, K., et al., *Lifespan extension and delayed immune and collagen aging in mutant mice with defects in growth hormone production.* Proc Natl Acad Sci USA, 2001. 98(12): p. 6736-41.
13. Brown-Borg, H. M. and S. G. Rakoczy, *Catalase expression in delayed and premature aging mouse models.* Exp Gerontol, 2000. 35(2): p. 199-212.
14. Brown-Borg, H. M., et at, *Effects of growth hormone and insulin-like growth factor-1 on hepatocyte antioxidative enzymes.* Exp Biol Med (Maywood), 2002. 227(2): p. 94-104.
15. Murakami, S., *Stress resistance in long-lived mouse models.* Exp Gerontol, 2006. 41(10): p. 1014-9.
16. Sharma, H. S., et al., *Neurotrophic factors influence upregulation of constitutive isoform of heme oxygenase and cellular stress response in the spinal cord following trauma. An experimental study using immunohistochemistry in the rat.* Amino Acids, 2000. 19(1): p. 351-61.
17. Li, Y., et al., *SirT1 inhibition reduces IGF-I/IRS-2/Ras/ERK1/2 signaling and protects neurons.* Cell Metab, 2008. 8(1): p. 38-48.
18. Fabrizio, P., et al., *SOD2 functions downstream of Sch9 to extend longevity in yeast.* Genetics, 2003. 163(1): p. 35-46.
19. Fabrizio, P., et al., *Regulation of longevity and stress resistance by Sch9 in yeast.* Science, 2001. 292(5515): p. 288-90.
20. Longo, V. D., et at, *Human Bcl-2 reverses survival defects in yeast lacking superoxide dismutase and delays death of wild-type yeast.* J Cell Biol, 1997. 137(7): p. 1581-8.
21. Wei, M., et al., *Life span extension by calorie restriction depends on Rim15 and transcription factors downstream of Ras/PKA, Tor, and Sch9.* PLoS Genet, 2008. 4(1): p. e13.
22. Yan, L., et al., *Type 5 adenylyl cyclase disruption increases longevity and protects against stress.* Cell, 2007. 130(2): p. 247-58.
23. Longo, V. D. and C. E. Finch, *Evolutionary medicine: from dwarf model systems to healthy centenarians?* Science, 2003. 299(5611): p. 1342-6.
24. Kandel, E. S. and N. Hay, *The regulation and activities of the multifunctional serine/threonine kinase Akt/PKB.* Exp Cell Res, 1999. 253(1): p. 210-29.
25. Pollak, M. N., E. S. Schernhammer, and S. E. Hankinson, *Insulin-like growth factors and neoplasia.* Nat Rev Cancer, 2004. 4(7): p. 505-18.
26. Guevara-Aguirre, J., et al., *Growth hormone receptor deficiency is associated with a major reduction in pro-aging signaling, cancer, and diabetes in humans.* Sci Transl Med, 2011. 3(70): p. 70ra13.
27. Kopchick, J. J., *Discovery and development of a new class of drugs: GH antagonists.* J Endocrinol Invest, 2003. 26(10 Suppl): p. 16-26.
28. Raffaghello, L., et al., *Starvation-dependent differential stress resistance protects normal but not cancer cells against high-dose chemotherapy.* Proc Natl Acad Sci USA, 2008. 105(24): p. 8215-20.
29. Maxwell, S. R. and G. Y. Lip, *Reperfusion injury: a review of the pathophysiology, clinical manifestations and therapeutic options.* Int J Cardiol, 1997. 58(2): p. 95-117.
30. Flores-Morales, A., et al., *Negative regulation of growth hormone receptor signaling.* Mol Endocrinol, 2006. 20(2): p. 241-53.
31. Wormald, S. and D. J. Hilton, *Inhibitors of cytokine signal transduction.* J Biol Chem, 2004. 279(2): p. 821-4.
32. Hodge, C., et al., *Growth hormone stimulates phosphorylation and activation of elk-1 and expression of c-fos, egr-1, and junB through activation of extracellular signal-regulated kinases 1 and 2.* J Biol Chem, 1998. 273 (47): p. 31327-36.

---

What is claimed is:

1. A compound having formula I:

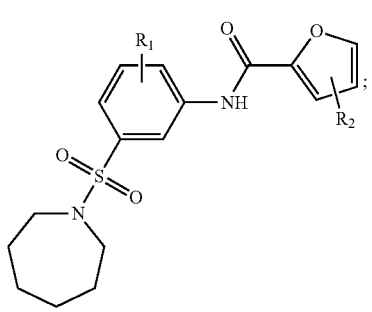

or a pharmaceutically acceptable salt thereof;
wherein:
   $R_1$ is $NO_2$, $SO_3H$, $NH_2$, or halogen, and
   $R_2$ is hydrogen, $NO_2$, $SO_3H$, $NH_2$, or $C_{1-8}$ alkyl, or halogen.

2. A compound having formula II:

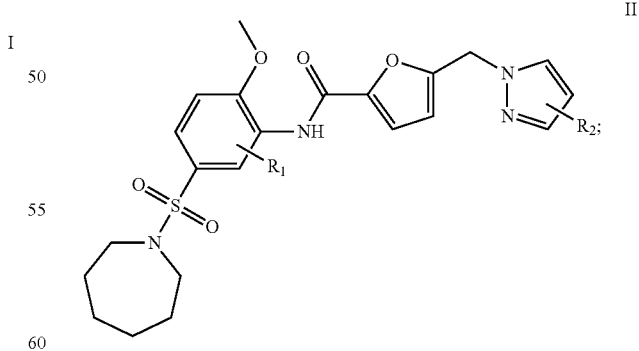

or a pharmaceutically acceptable salt thereof;
wherein:
   $R_1$ is hydrogen, $C_{1-8}$ alkyl, or halogen, and
   $R_2$ is $C_{1-8}$ alkyl, or halogen.

3. A method inhibiting GH induced phosphorylation STAT5, the method comprising:

administering to a subject a therapeutically effective amount of a compound selected from the group consisting of:

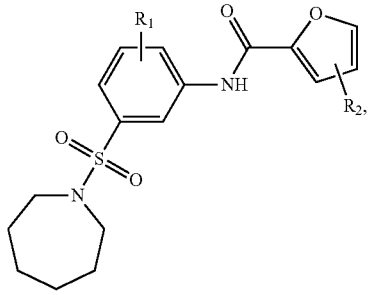
I

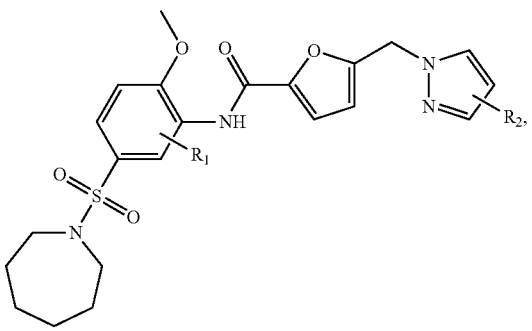
II

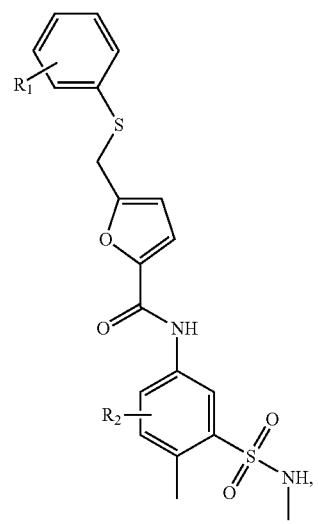
III

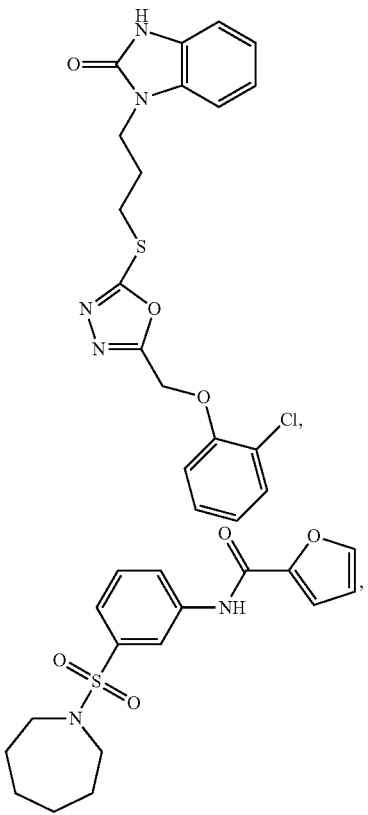

and combinations thereof and pharmaceutically acceptable salts thereof;

wherein:
R$_1$ is hydrogen, NO$_2$, SO$_3$H, NH$_3$, C$_{1-8}$ alkyl, or halogen, and
R$_2$ is hydrogen, NO$_2$, SO$_3$H, NH$_3$, C$_{1-8}$ alkyl, or halogen.

4. The method of claim 3 wherein the compound is selected from the group consisting of:

-continued

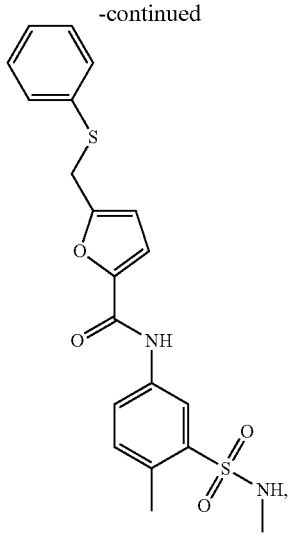

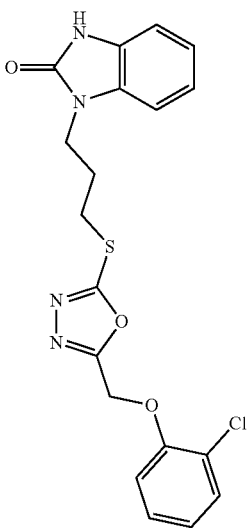 [SMILES: O=c1[nH]c2ccccc2n1CCCSc1nnc(COc2ccccc2Cl)o1]

and pharmaceutically acceptable salts thereof.

10. The method of claim 3 wherein the compound is selected from the group consisting of:

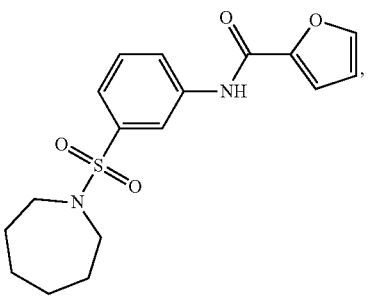 [SMILES: O=C(Nc1cccc(S(=O)(=O)N2CCCCCC2)c1)c1ccco1]

and pharmaceutically acceptable salts thereof.

11. The method of claim 3 wherein the compound is selected from the group consisting of:

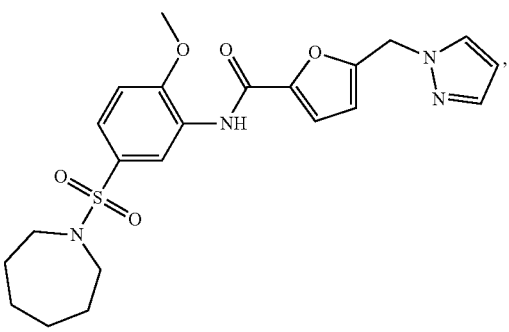 [SMILES: COc1ccc(S(=O)(=O)N2CCCCCC2)cc1NC(=O)c1ccc(Cn2cccn2)o1]

and pharmaceutically acceptable salts thereof.

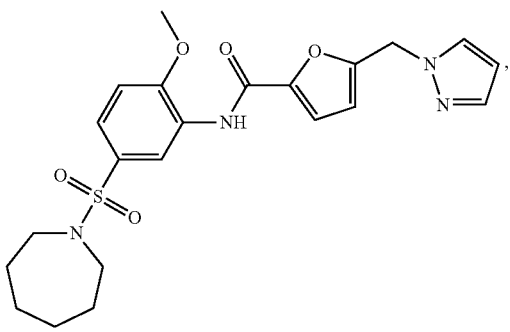

and combinations thereof, and pharmaceutically acceptable salts thereof.

5. The compound of claim 1 wherein $R_1$ is $NO_2$ or $SO_3H$ and $R_2$ is hydrogen or $C_{1-8}$ alkyl.

6. The compound of claim 1 wherein $R_1$ is $NH_2$ or halogen and $R_2$ is hydrogen or $C_{1-8}$ alkyl.

7. The method of claim 3 wherein is hydrogen.

8. The method of claim 3 wherein $R_2$ is hydrogen.

9. The method of claim 3 wherein the compound is selected from the group consisting of:

* * * * *

UNITED STATES PATENT AND TRADEMARK OFFICE
CERTIFICATE OF CORRECTION

PATENT NO. : 10,246,446 B2
APPLICATION NO. : 14/913130
DATED : April 2, 2019
INVENTOR(S) : Valter D. Longo et al.

It is certified that error appears in the above-identified patent and that said Letters Patent is hereby corrected as shown below:

In the Specification

Column 1, Line 17:
After "STATEMENT REGARDING FEDERALLY SPONSORED RESEARCH OR DEVELOPMENT", Delete:
"This invention was made with Government support under Contract No. 5P01AGO34906-04 awarded by the National Institute of Health. The Government has certain rights to the invention."
And Insert:
--This invention was made with government support under Grant No. AG034906, awarded by the National Institutes of Health. The government has certain rights in the invention.--

Signed and Sealed this
Thirtieth Day of January, 2024

Katherine Kelly Vidal
*Director of the United States Patent and Trademark Office*

SEQUENCE LISTING

```
<160> NUMBER OF SEQ ID NOS: 9

<210> SEQ ID NO 1
<211> LENGTH: 650
<212> TYPE: PRT
<213> ORGANISM: Homo sapiens

<400> SEQUENCE: 1

Met Asp Leu Cys Gln Val Phe Leu Thr Leu Ala Leu Ala Val Thr Ser
1               5                   10                  15

Ser Thr Phe Ser Gly Ser Glu Ala Thr Pro Ala Thr Leu Gly Lys Ala
            20                  25                  30

Ser Pro Val Leu Gln Arg Ile Asn Pro Ser Leu Gly Thr Ser Ser Ser
        35                  40                  45

Gly Lys Pro Arg Phe Thr Lys Cys Arg Ser Pro Glu Leu Glu Thr Phe
    50                  55                  60

Ser Cys Tyr Trp Thr Glu Gly Asp Asn Pro Asp Leu Lys Thr Pro Gly
65                  70                  75                  80
```

```
Ser Ile Gln Leu Tyr Tyr Ala Lys Arg Glu Ser Gln Arg Gln Ala Ala
                85                  90                  95

Arg Ile Ala His Glu Trp Thr Gln Glu Trp Lys Glu Cys Pro Asp Tyr
            100                 105                 110

Val Ser Ala Gly Lys Asn Ser Cys Tyr Phe Asn Ser Ser Tyr Thr Ser
            115                 120                 125

Ile Trp Ile Pro Tyr Cys Ile Lys Leu Thr Thr Asn Gly Asp Leu Leu
            130                 135                 140

Asp Gln Lys Cys Phe Thr Val Asp Glu Ile Val Gln Pro Asp Pro Pro
145                 150                 155                 160

Ile Gly Leu Asn Trp Thr Leu Leu Asn Ile Ser Leu Thr Gly Ile Arg
                165                 170                 175

Gly Asp Ile Gln Val Ser Trp Gln Pro Pro Asn Ala Asp Val Leu
            180                 185                 190

Lys Gly Trp Ile Ile Leu Glu Tyr Glu Ile Gln Tyr Lys Glu Val Asn
            195                 200                 205

Glu Ser Lys Trp Lys Val Met Gly Pro Ile Trp Leu Thr Tyr Cys Pro
    210                 215                 220

Val Tyr Ser Leu Arg Met Asp Lys Glu His Glu Val Arg Val Arg Ser
225                 230                 235                 240

Arg Gln Arg Ser Phe Glu Lys Tyr Ser Glu Phe Ser Glu Val Leu Arg
                245                 250                 255

Val Ile Phe Pro Gln Thr Asn Ile Leu Glu Ala Cys Glu Glu Asp Ile
            260                 265                 270

Gln Phe Pro Trp Phe Leu Ile Ile Ile Phe Gly Ile Phe Gly Val Ala
            275                 280                 285

Val Met Leu Phe Val Val Ile Phe Ser Lys Gln Gln Arg Ile Lys Met
            290                 295                 300

Leu Ile Leu Pro Pro Val Pro Val Pro Lys Ile Lys Gly Ile Asp Pro
305                 310                 315                 320

Asp Leu Leu Lys Glu Gly Lys Leu Glu Glu Val Asn Thr Ile Leu Gly
                325                 330                 335

Ile His Asp Asn Tyr Lys Pro Asp Phe Tyr Asn Asp Asp Ser Trp Val
            340                 345                 350

Glu Phe Ile Glu Leu Asp Ile Asp Glu Ala Asp Val Asp Glu Lys Thr
            355                 360                 365

Glu Gly Ser Asp Thr Asp Arg Leu Leu Ser Asn Asp His Glu Lys Ser
            370                 375                 380

Ala Gly Ile Leu Gly Ala Lys Asp Asp Ser Gly Arg Thr Ser Cys
385                 390                 395                 400

Tyr Asp Pro Asp Ile Leu Asp Thr Asp Phe His Thr Ser Asp Met Cys
            405                 410                 415

Asp Gly Thr Leu Lys Phe Arg Gln Ser Gln Lys Leu Asn Met Glu Ala
            420                 425                 430

Asp Leu Leu Cys Leu Asp Gln Lys Asn Leu Lys Asn Leu Pro Tyr Asp
            435                 440                 445

Ala Ser Leu Gly Ser Leu His Pro Ser Ile Thr Gln Thr Val Glu Glu
            450                 455                 460

Asn Lys Pro Gln Pro Leu Leu Ser Ser Glu Thr Glu Ala Thr His Gln
465                 470                 475                 480

Leu Ala Ser Thr Pro Met Ser Asn Pro Thr Ser Leu Ala Asn Ile Asp
                485                 490                 495

Phe Tyr Ala Gln Val Ser Asp Ile Thr Pro Ala Gly Gly Asp Val Leu
```

-continued

```
                500             505             510
Ser Pro Gly Gln Lys Ile Lys Ala Gly Ile Ala Gln Gly Asn Thr Gln
            515                 520                 525

Arg Glu Val Ala Thr Pro Cys Gln Glu Asn Tyr Ser Met Asn Ser Ala
        530                 535                 540

Tyr Phe Cys Glu Ser Asp Ala Lys Lys Cys Ile Ala Val Ala Arg Arg
545                 550                 555                 560

Met Glu Ala Thr Ser Cys Ile Lys Pro Ser Phe Asn Gln Glu Asp Ile
                565                 570                 575

Tyr Ile Thr Thr Glu Ser Leu Thr Thr Thr Ala Gln Met Ser Glu Thr
            580                 585                 590

Ala Asp Ile Ala Pro Asp Ala Glu Met Ser Val Pro Asp Tyr Thr Thr
                595                 600                 605

Val His Thr Val Gln Ser Pro Arg Gly Leu Ile Leu Asn Ala Thr Ala
        610                 615                 620

Leu Pro Leu Pro Asp Lys Lys Asn Phe Pro Ser Ser Cys Gly Tyr Val
625                 630                 635                 640

Ser Thr Asp Gln Leu Asn Lys Ile Met Gln
                645                 650

<210> SEQ ID NO 2
<211> LENGTH: 12
<212> TYPE: PRT
<213> ORGANISM: Homo sapiens

<400> SEQUENCE: 2

Thr Glu Gly Asp Asn Pro Asp Leu Lys Thr Pro Gly
1               5                   10

<210> SEQ ID NO 3
<211> LENGTH: 12
<212> TYPE: PRT
<213> ORGANISM: Homo sapiens

<400> SEQUENCE: 3

Glu Ser Lys Trp Lys Val Met Gly Pro Ile Trp Leu
1               5                   10

<210> SEQ ID NO 4
<211> LENGTH: 12
<212> TYPE: PRT
<213> ORGANISM: Homo sapiens

<400> SEQUENCE: 4

Lys Leu Thr Thr Asn Gly Asp Leu Leu Asp Gln Lys
1               5                   10

<210> SEQ ID NO 5
<211> LENGTH: 12
<212> TYPE: PRT
<213> ORGANISM: Homo sapiens
```

```
<400> SEQUENCE: 5

Arg Ser Phe Glu Lys Tyr Ser Glu Phe Ser Glu Val
1               5                   10

<210> SEQ ID NO 6
<211> LENGTH: 12
<212> TYPE: PRT
<213> ORGANISM: Homo sapiens

<400> SEQUENCE: 6

Thr Val Asp Glu Ile Val Gln Pro Asp Pro Pro Ile
1               5                   10

<210> SEQ ID NO 7
<211> LENGTH: 12
<212> TYPE: PRT
<213> ORGANISM: Homo sapiens

<400> SEQUENCE: 7

Thr Leu Leu Asn Ile Ser Leu Thr Gly Ile Arg Gly
1               5                   10

<210> SEQ ID NO 8
<211> LENGTH: 12
<212> TYPE: PRT
<213> ORGANISM: Homo sapiens

<400> SEQUENCE: 8

Glu Tyr Glu Ile Gln Tyr Lys Glu Val Asn Glu Ser
1               5                   10

<210> SEQ ID NO 9
<211> LENGTH: 12
<212> TYPE: PRT
<213> ORGANISM: Homo sapiens

<400> SEQUENCE: 9

Pro Val Tyr Ser Leu Arg Met Asp Lys Glu His Glu
1               5                   10
```